US008909481B2

(12) United States Patent
Goodlett

(10) Patent No.: US 8,909,481 B2
(45) Date of Patent: Dec. 9, 2014

(54) METHOD OF MASS SPECTROMETRY FOR IDENTIFYING POLYPEPTIDES

(75) Inventor: David R. Goodlett, Seattle, WA (US)

(73) Assignee: The Institute of Systems Biology, Seattle, WA (US)

(*) Notice: Subject to any disclaimer, the term of this patent is extended or adjusted under 35 U.S.C. 154(b) by 1207 days.

(21) Appl. No.: 11/225,265

(22) Filed: Sep. 12, 2005

(65) Prior Publication Data
US 2006/0009915 A1    Jan. 12, 2006

Related U.S. Application Data

(63) Continuation of application No. 09/748,783, filed on Dec. 26, 2000, now abandoned.

(51) Int. Cl.
G01N 33/48 (2006.01)
G01N 33/68 (2006.01)

(52) U.S. Cl.
CPC .................. G01N 33/6803 (2013.01)
USPC ........................................ 702/19

(58) Field of Classification Search
None
See application file for complete search history.

(56) References Cited

U.S. PATENT DOCUMENTS

| | | | |
|---|---|---|---|
| 4,851,669 A | 7/1989 | Aberth | |
| 5,036,014 A | 7/1991 | ElSohly et al. | |
| 5,073,713 A | 12/1991 | Smith et al. | |
| 5,179,196 A | 1/1993 | Johnson et al. | |
| 5,298,743 A | 3/1994 | Kato | |
| 5,538,897 A | 7/1996 | Yates, III et al. | |
| 5,661,298 A | 8/1997 | Bateman | |
| 5,703,360 A | 12/1997 | Fischer et al. | |
| 5,744,798 A | 4/1998 | Kato | |
| 5,869,830 A | 2/1999 | Franzen et al. | |
| 5,885,841 A | 3/1999 | Higgs, Jr. et al. | |
| 5,910,655 A | 6/1999 | Skilling | |
| 6,002,130 A | 12/1999 | Kato | |
| 6,017,693 A | 1/2000 | Yates, III et al. | |
| 6,087,657 A | 7/2000 | Kato | |
| 6,107,623 A | 8/2000 | Bateman et al. | |
| 6,188,064 B1 | 2/2001 | Koster | |
| 6,204,500 B1 | 3/2001 | Whitehouse et al. | |
| 6,225,047 B1 | 5/2001 | Hutchens et al. | |
| 6,322,970 B1 | 11/2001 | Little et al. | |
| 6,323,482 B1 | 11/2001 | Clemmer et al. | |
| 6,329,652 B1 | 12/2001 | Windig et al. | |
| 6,331,702 B1 | 12/2001 | Krutchinsky et al. | |
| 6,348,688 B1 | 2/2002 | Vestal | |
| 6,373,051 B1 | 4/2002 | Hayakawa et al. | |
| 6,489,121 B1 | 12/2002 | Skilling | |
| 6,489,608 B1 | 12/2002 | Skilling | |
| 6,570,153 B1 | 5/2003 | Li et al. | |
| 6,579,719 B1 | 6/2003 | Hutchens et al. | |
| 6,586,727 B2 | 7/2003 | Bateman et al. | |
| 6,590,203 B2 | 7/2003 | Kato | |
| 6,670,606 B2 | 12/2003 | Verentchikov et al. | |
| 6,675,104 B2 | 1/2004 | Paulse et al. | |
| 6,717,130 B2 | 4/2004 | Bateman et al. | |
| 6,744,040 B2 | 6/2004 | Park | |
| 6,794,640 B2 | 9/2004 | Bateman et al. | |
| 6,811,969 B1 | 11/2004 | Hutchens et al. | |
| 6,818,411 B2 | 11/2004 | Hutchens et al. | |
| 6,835,927 B2 | 12/2004 | Becker et al. | |
| 6,844,165 B2 | 1/2005 | Hutchens et al. | |
| 6,881,586 B2 | 4/2005 | Hutchens et al. | |
| 6,906,319 B2 | 6/2005 | Hoyes | |
| 6,965,106 B2 | 11/2005 | Ding et al. | |
| 6,982,414 B2 | 1/2006 | Bateman et al. | |
| 7,053,305 B2 | 5/2006 | Takase et al. | |
| 7,105,339 B2 | 9/2006 | Hutchens et al. | |
| 7,112,453 B2 | 9/2006 | Hutchens et al. | |
| 7,112,784 B2 | 9/2006 | Bateman et al. | |
| 7,160,734 B2 | 1/2007 | Hutchens et al. | |
| 7,196,326 B2 | 3/2007 | Franzen et al. | |
| 7,202,473 B2 | 4/2007 | Bateman et al. | |
| 7,230,235 B2 | 6/2007 | Goldberg et al. | |
| 7,329,484 B2 | 2/2008 | Hutchens et al. | |
| 7,365,309 B2 | 4/2008 | Denny et al. | |
| 7,388,197 B2 | 6/2008 | McLean et al. | |

(Continued)

FOREIGN PATENT DOCUMENTS

EP    898297 A2    2/1999
EP    1006559 A2    6/2000

(Continued)

OTHER PUBLICATIONS

Hunt et al., Clinical Chemistry, 1982, vol. 28, No. 12, p. 2387-2392.*

(Continued)

Primary Examiner — Pablo S Whaley
(74) Attorney, Agent, or Firm — Diederiks & Whitelaw, PLC

(57) ABSTRACT

The invention provides methods for identifying polypeptides. The method can include the steps of simultaneously determining the mass of a subset of parent polypeptides from a population of polypeptides and the mass of fragments of the subset of parent polypeptides; comparing the determined masses to an annotated polypeptide index; and identifying one or more polypeptides of the annotated polypeptide index having the determined masses. The method can further include the steps of determining one or more additional characteristics associated with one or more of the parent polypeptides; comparing the determined characteristics to the annotated polypeptide index; and optionally repeating the steps one or more times, wherein a set of characteristics is determined that identifies a parent polypeptide as a single polypeptide in the annotated polypeptide index. The method can additionally include the step of quantitating the amount of the identified polypeptide in a sample containing the polypeptide.

13 Claims, 5 Drawing Sheets

(56) References Cited

U.S. PATENT DOCUMENTS

| | | |
|---|---|---|
| 7,417,226 B2 | 8/2008 | Bajic et al. |
| 7,473,892 B2 | 1/2009 | Sano et al. |
| 7,534,622 B2 | 5/2009 | Hunt et al. |
| 7,595,484 B2 | 9/2009 | Yokosuka et al. |
| 7,608,819 B2 | 10/2009 | Baba et al. |
| 7,645,984 B2 | 1/2010 | Gorenstein et al. |
| 7,683,314 B2 | 3/2010 | Green et al. |
| 7,759,638 B2 | 7/2010 | Makarov |
| 7,825,374 B2 | 11/2010 | Cotter et al. |
| 7,928,363 B2 | 4/2011 | Bateman |
| 2001/0014461 A1 | 8/2001 | Hutchens et al. |
| 2001/0052569 A1 | 12/2001 | Bateman et al. |
| 2002/0014586 A1 | 2/2002 | Clemmer |
| 2002/0053545 A1 | 5/2002 | Greef |
| 2002/0063206 A1 | 5/2002 | Bateman et al. |
| 2002/0115056 A1 | 8/2002 | Goodlett |
| 2002/0119490 A1 | 8/2002 | Aebersold |
| 2002/0123043 A1 | 9/2002 | Hutchens et al. |
| 2002/0142343 A1 | 10/2002 | Hutchens et al. |
| 2002/0155509 A1 | 10/2002 | Hutchens et al. |
| 2002/0175280 A1 | 11/2002 | Franzen et al. |
| 2002/0177242 A1 | 11/2002 | Hutchens et al. |
| 2003/0040123 A1 | 2/2003 | Hastings |
| 2003/0096224 A1 | 5/2003 | Hutchens et al. |
| 2004/0041091 A1 | 3/2004 | Bateman et al. |
| 2004/0137427 A1 | 7/2004 | Hutchens et al. |
| 2004/0142493 A1 | 7/2004 | Hutchens et al. |
| 2004/0155180 A1 | 8/2004 | Zubarev |
| 2004/0180446 A1 | 9/2004 | Thompson et al. |
| 2004/0188603 A1 | 9/2004 | Bateman et al. |
| 2004/0245452 A1 | 12/2004 | Bateman et al. |
| 2005/0092910 A1 | 5/2005 | Geromanos et al. |
| 2005/0092911 A1 | 5/2005 | Hoyes |
| 2005/0199804 A1 | 9/2005 | Hunt et al. |
| 2005/0233306 A1 | 10/2005 | Hutchens et al. |
| 2005/0279931 A1 | 12/2005 | Franzen et al. |
| 2006/0008851 A1 | 1/2006 | Aebersold et al. |
| 2006/0009915 A1 | 1/2006 | Goodlett |
| 2006/0024720 A1 | 2/2006 | McLean et al. |
| 2006/0169889 A1 | 8/2006 | Yokosuka et al. |
| 2007/0042414 A1 | 2/2007 | Hutchens et al. |
| 2007/0114439 A1 | 5/2007 | Bajic et al. |
| 2007/0278397 A1 | 12/2007 | Bateman et al. |
| 2007/0284521 A1 | 12/2007 | Green et al. |
| 2008/0044915 A1 | 2/2008 | Hunt et al. |
| 2008/0135746 A1 | 6/2008 | Wildgoose et al. |
| 2008/0224033 A1 | 9/2008 | Makarov |
| 2009/0065690 A1 | 3/2009 | Bateman |
| 2009/0173877 A1 | 7/2009 | Bateman et al. |
| 2009/0194688 A1 | 8/2009 | Bateman et al. |
| 2009/0206248 A1 | 8/2009 | Makarov et al. |
| 2009/0272895 A1 | 11/2009 | Makarov |
| 2009/0294645 A1 | 12/2009 | Gorenstein et al. |
| 2011/0057095 A1 | 3/2011 | Loboda |

FOREIGN PATENT DOCUMENTS

| | | |
|---|---|---|
| EP | 1043676 A2 | 10/2000 |
| EP | 1047107 A2 | 10/2000 |
| EP | 1225618 A2 | 7/2002 |
| EP | 1564783 A2 | 8/2005 |
| EP | 1598666 A1 | 11/2005 |
| EP | 1638133 A2 | 3/2006 |
| EP | 2053632 A2 | 4/2009 |
| GB | 2120007 A | 11/1983 |
| GB | 2300967 A | 11/1996 |
| GB | 2347012 A | 8/2000 |
| GB | 2363249 A | 12/2001 |
| GB | 2364168 A | 1/2002 |
| GB | 2391699 A | 2/2004 |
| GB | 2392303 A | 2/2004 |
| GB | 2394545 A | 4/2004 |
| GB | 2405991 A | 3/2005 |
| JP | 61-272651 | 12/1986 |
| JP | S62-168331 | 7/1987 |
| JP | S64-86437 | 3/1989 |
| JP | H02-158048 | 6/1990 |
| JP | H04-171650 | 6/1992 |
| JP | H05-500726 | 2/1993 |
| JP | H05-121042 | 5/1993 |
| JP | H07-6730 | 1/1995 |
| JP | H07-211282 | 8/1995 |
| JP | H08-124519 | 5/1996 |
| JP | H10-12188 | 1/1998 |
| JP | H10501095 | 1/1998 |
| JP | H11-154486 | 6/1999 |
| JP | H11-288683 | 10/1999 |
| JP | H11-512518 | 10/1999 |
| JP | 2000241390 A | 9/2000 |
| JP | 2002502085 A | 1/2002 |
| JP | 2002100318 A | 4/2002 |
| JP | 2002110081 A | 4/2002 |
| JP | 2002241390 A | 8/2002 |
| JP | 2002544517 A | 12/2002 |
| JP | 2003530675 A | 10/2003 |
| JP | 2003315313 A | 11/2003 |
| JP | 2005502175 A | 1/2005 |
| JP | 2005235412 A | 9/2005 |
| WO | WO-8912314 A1 | 12/1989 |
| WO | WO-9748120 A1 | 12/1997 |
| WO | WO-9806481 A1 | 2/1998 |
| WO | WO/98/21326 * | 5/1998 |
| WO | WO 98/59360 | 12/1998 |
| WO | WO 98/59361 | 12/1998 |
| WO | WO 98/59362 | 12/1998 |
| WO | WO-9901889 A1 | 1/1999 |
| WO | WO 99/12040 | 3/1999 |
| WO | WO 99/16103 | 4/1999 |
| WO | WO-9938185 A2 | 7/1999 |
| WO | WO-9938193 A1 | 7/1999 |
| WO | WO-9962101 A1 | 12/1999 |
| WO | WO 00/11208 | 3/2000 |
| WO | WO-0018496 A1 | 4/2000 |
| WO | WO 00/70648 | 11/2000 |
| WO | WO-0178106 A2 | 10/2001 |
| WO | WO-0248699 A2 | 6/2002 |
| WO | WO-02078046 A2 | 10/2002 |
| WO | WO-02096540 A1 | 12/2002 |
| WO | WO-03021631 A2 | 3/2003 |
| WO | WO-03095978 A2 | 11/2003 |
| WO | WO-03102545 A2 | 12/2003 |
| WO | WO-2004008481 A1 | 1/2004 |
| WO | WO-2004046731 A2 | 6/2004 |
| WO | WO-2004049385 A2 | 6/2004 |
| WO | WO-2004077488 A2 | 9/2004 |
| WO | WO-2004107388 A2 | 12/2004 |
| WO | WO-2005090978 A1 | 9/2005 |
| WO | WO-2005114930 A2 | 12/2005 |
| WO | WO-2006003429 A2 | 1/2006 |

OTHER PUBLICATIONS

Perkins et al., Electrophoresis, 1999, vol. 20, p. 3551-3567.*
Green et al., Analytical Biochemistry, 1999, vol. 275, p. 39-46.*
Wilkins et al., Journal of Theoretical Biology, 1997, vol. 186, p. 7-15.*
Figey et al. (Analytical Chemistry, May 1999, vol. 71, No. 13, p. 2279-2287).*
Masselon et al. (Anal. Chem., Mar. 2000, 72:1918-1924).*
Page et al. (PNAS, Oct. 1999, 96, 22: 12589-12594).*
Purvice et al. (Proteomics, 2003, 3, 847-850).*
Yates et al. (Journal of Mass Spectrometry, 1998, vol. 33, pp. 1-19).*
Hoffman (Journal of Mass Spectrometry, 1996, vol. 31, pp. 129-137).*
Aebersold et al., "Towards an integrated analytical technology for the generation of multidimensional protein expression maps," *J. Protein Chem.*, 17(6):533-535 (1998).
Brockstedt et al., "Identification of apoptosis-associated proteins in human burkitt lymphoma cell line," *J. Biol. Chem.*, 273:28057-28064 (1998).
Bruce et al., "High-mass-measurement accuracy and 100% sequence coverage of enzymatically digested bovine serum albumin from an

(56) References Cited

OTHER PUBLICATIONS

ESI-FTICR mass spectrum," *Analytical Chem.*, 71:2595-2599 (1999).
The *C elegans* Sequencing Consortium, "Genome sequence of the nematode *C. elegans*: a platform for investigating biology," *Science* 282:2012-2018 (1998).
Clauser et al., "Rapid mass spectrometric peptide sequencing and mass matching for characterization of human melanoma proteins isolated by two-dimensional PAGE," *Proc. Natl. Acad. Sci. USA* 92-5072-5076 (1995).
Constanzo et al., "The yeast proteome database (YPD) and *caenorhabditis elegans* proteome database (WormPD): comprehensive resources for the organization and comparison of model organism protein information," *Nucleic Acids Res.* 28(1):73-76 (2000).
Corthals et al., "Identification of proteins by mass spectrometry," *Proteome Res.: 2D. Gel Electro.Detec. Metho.* Ch, 10., Ed. Rabilloud, T., Springer, New York, pp. 1-17 (1999).
Courchesne and Patterson, "Identification of proteins by Matrix-assisted laser desription/ionization mass spectrometry using peptide and fragment ion masses," *Meth. Mol. Biol.* 112:487-511 (1999).
Dalmasso, "Discovery of protein biomarkers and "Phenomic Fingerprints" using SELDI ProteinChip® systems," *Life Science On-line*, (1999) (printed from http://www.ciphergen.com//bio.html on Jun. 7, 2001).
De Leenheer et al., "Applications of isotope dilution-mass spectrometry in clinical chemistry, pharmacokinetics and toxicology," *Mass. Spectrom. Reviews*, 11:249-307 (1992).
Ducret et al., "High throughput protein characterization by automated reverse-phase chromatography/electrospray tandem mass spectrometry" *Protein Sciences*, 7(3):706-719 (1998).
Easterling et al., "Routine part-per-million mass accuracy for high-mass ions: space-charge effects in MALDI FT-ICR," *Analytical Chem.*, 71:624-632 (1999).
Eng et al., "An approach to correlate tandem mass spectral data peptides with amino acid sequence in a protein database," *J. Am. Soc. Mass. Spectrom.*, 5:976-989 (1994).
Erdjument-Bromage et al., "Examination of micro-tip reversed-phase liquid chromatographic extraction of peptide pools for mass spectrometric analysis," *J. Chromatogr. A.*, 826:167-181 (1998).
Goodlett et al., "Protein identification with a single accurate mass of a cysteine-containing peptide and constrained database searching" *Anal. Chem.* 72(6):1112-1118 (2000).
Gygi et al., "Correlation between protein and mRNA abundance in yeast" *Mol. Cell Biol.* 19(3):1720-1730 (1999).
Gygi et al., "Quantitative analysis of complex protein mixtures using isotope-coded affinity tags," *Nat. Biotechnol.*, 17(10):994-999 (1999).
Gygi et al., "Evaluation of two-dimensional gel electrophoresis based proteome analysis technology" *Proc. Natl. Acad. Sci. USA.*, 97:9390-9395 (2000).
Henzel et al., "Identifying proteins from two dimensional gels by molecular mass searching of peptide fragments in protein sequence databases," *Proc. Natl. Acad. Sci. USA* 90:5011-5015 (1993).
Hutchens and Yip, "New desorption strategies for the mass spectrometric analysis of macromolecules," *Rapid Commun. Mass Spectrom.*, 7:576-580 (1993).
Jensen et al., "Mass spectrometric identification and microcharacterization of proteins from electrophoretic gels: strategies and applications," *Proteins: Struct. Funct. Genet., Suppl.* 2:74-89 (1998).
Kuwata et al., "Bacterial domain of lactoferrin: detection, quantitation, and characterization of lactoferricin in serum by SELDI affinity mass spectrometry," *Biochemical Biophysical Research Communications*, 245:764-773 (1998).
Kuwata et al., "Direct detection and quantitative determination of bovine lactoferricin and lactoferrin fragments in human gastric contents by affinity mass spectrometry," *Advances in Experimental Medicine Biology*, 443:23-32 (1998).
Link et al., "Direct analysis of protein complexes using mass spectrometry," *Nature Biotechnology*, 17:676-682 (1999).
Mann, M., "Quantitative proteomics?" *Nat. Biotechnol.* 17:954-955 (1999).
Masselon et al., "Accurate mass multiplexed tandem mass spectrometry for high-throughput polypeptide identification from mixtures," *Anal. Chem.*, 72:1918-1924 (2000).
Merchant and Weinberger, "Recent advancements in surface-enhanced laser desorption/ionization-time of flight-mass spectrometry," *Electrophoresis*, 21:1164-1167 (2000).
MOWSE peptide database contents, 1993.
Oda et al., "Accurate quantitation of protein expression and site-specific phosphorylation" *Proc. Natl. Acad. Sci. USA*, 96:6591-6596 (1999).
OWL protein database contents, Nov. 30, 1998.
Patterson and Aebersold, "Mass spectrometric approaches for identification of gel-separated proteins," *Electrophoresis*, 16:1791-1814 (1995).
Paweletz et al., "Rapid protein display profiling of cancer progression directly from human tissue using a protein biochip," *Drug Development Research*, 49:34-42 (2000).
Pennington et al., Proteome analysis: from protein characterization to biological function, *Trends Cell Biol.* 7:168-173 (1997).
Soukhanov and Ellis, Editors, *Webster's New Riverside University Dictionary*, The Riverside Publishing Company, p. 428.
Traini et al., "Towards an automated approach for protein identification in proteome projects," *Electrophoresis*, 19:1941-1949 (1998).
Voivodov et al., "Surface arrays of energy absorbing polymers enabling covalent attachment of biomolecules for subsequent laser-induced uncouplin/desorption," *Tetrahedron Lett.*, 37:5669-5672 (1996).
Weiss et al., "Rapid and sensitive fingerprinting of wine proteins by matrix-assisted laser desorption/ionization time-of-flight (MALDI-TOF)," *Am. J. Enol. Vitic.*, 49:231-239 (1998).
Wright et al., "ProteinChip® surface enhanced laser desorption/ionization (SELDI) mass spectrometry: a novel protein biochip technology for detection of prostate cancer biomarkers in complex protein mixtures," *Prostate Cancer Prostetic Diseases*, 2:264-276 (2000).
Yates J., "Database searching using mass spectrometry data," *Electrophoresis*, 19:893-900 (1998).
Yates J., "Mass spectrometry and the age of the proteome," *J. Mass Spectrometry*, 33:1-19 (1998).
Yates et al., "Automated protein identification using microcolumn liquid chromatography-tandem mass spectrometry," *Methods Mol. Biol.*, 112:553-569 (1999).
Chen et al., "Identification of proteins from two-dimensional gel electrophoresis of human erythroleukemia cells using capillary high performance liquid chromatography/electrospray-ion trap-reflectron time-of-flight mass spectrometry with two-dimensional topographic map analysis of in-gel tryptic digest products," *Rapid Commun. Mass. Spectrom.* 13:1907-1916 (1999).
Geng et al., "Proteomics of glycoproteins based on affinity selection of glycopeptides from tryptic digests" *J. Chromatogr. B Biomed. Sci. Appl.* 752:293-306 (2001).
Kawano et al., "Rapid isolation and identification of staphylococcal exoproteins by reverse phase capillary high performance liquid chromatography-electrospray ionization mass spectrometry" FEMS Microbiol. Lett. 189:103-108 (2000).
O'Shannessy and Hoffman, "Site-directed immobilization of glycoproteins on hydrazide-containing solid supports" *Biotechnol. Appl. Biochem.* 9:488-496 (1987).
Qian et al., "Direct analysis of the products of sequential cleavages of peptides and proteins affinity-bound to immobilized metal ion beads by matrix-assisted laser desorption/ionization mass spectrometry" *Anal. Biochem.* 274:174-180 (1999).
Saito et al., "Computation program system for structural analysis and quantification of organic contaminants on silicon wafer surfaces from mass spectra" *Anal. Sciences* 16:563-596 (2000).
Snyder, "Automated Method Development in High-Performance Liquid Chromatography" *Meth. Enzymol.* 270:151-175 (1996).
Jones et al. "Analysis of bovine β-casein tryptic digest by continuous-flow fast-atom bombardment mass spectrometry" *Rapid Commun. Mass. Spectrom.* 5(4):192-195 (1991).

(56) References Cited

OTHER PUBLICATIONS

Kerns et al. "Buspirone metabolite structure profile using a standard liquid chromatographic-mass spectrometric protocol" *J. Chromatogr. B Biomed. Sci. Appl.* 698(1-2):133-145 (1997).
Raida et al. "Liquid chromatography and electrospray mass spectrometric mapping of peptides from human plasma filtrate" *J. Am. Soc. Mass. Spectrom.* 10(1):45-54 (1999).
Ginz and Engelhardt "Identification of praline-based diketopiperazines in roasted coffee" *J. Agric. Food Chem.* 48:3528-2532 (2000).
Poon et al., "Identification of 4-hydroxyandrost-4-ene-3, 17-dione metabolites in prostatic cancer patients by liquid chromatography-mass spectrometry" *J. Chromatog.* 576:235-244 (1992).
Advisory Action dated Aug. 28, 2003.
European Search Report dated Dec. 8, 2004 from European Application No. 01991551.
European Search Report dated Sep. 6, 2006 from European Application No. 06008833.3.
Final Office Action dated Aug. 5, 2008 from corresponding U.S. Appl. No. 11/223,269.
Final Office Action dated Jun. 24, 2011 from corresponding U.S. Appl. No. 11/223,269.
Final Office Action dated Jun. 9, 2005 from corresponding U.S. Appl. No. 09/748,793.
Final Office Action dated May 7, 2003 from corresponding U.S. Appl. No. 09/748,793.
Final Office Action dated Nov. 15, 2004 from corresponding U.S. Appl. No. 09/748,783.
Final Office Action dated Nov. 18, 2009 from corresponding U.S. Appl. No. 11/225,265.
Final Office Action dated Oct. 21, 2009 from corresponding U.S. Appl. No. 11/223,269.
Final Office Action dated Sep. 28, 2004 from corresponding U.S. Appl. No. 09/748,793.
Non Final Office Action dated Dec. 17, 2002 from corresponding U.S. Appl. No. 09/748,783.
Non Final Office Action dated Dec. 19, 2003 from corresponding U.S. Appl. No. 09/748,793.
Non Final Office Action dated Dec. 20, 2001 from corresponding U.S. Appl. No. 09/748,793.
Non Final Office Action dated Feb. 3, 2009 from corresponding U.S. Appl. No. 11/223,269.
Non Final Office Action dated Jul. 1, 2003 from corresponding U.S. Appl. No. 09/748,783.
Non Final Office Action dated Jun. 23, 2011 from corresponding U.S. Appl. No. 11/225,265.
Non Final Office Action dated Mar. 12, 2004 from corresponding U.S. Appl. No. 09/748,783.
Non Final Office Action dated Mar. 14, 2002 from corresponding U.S. Appl. No. 09/749,783.
Non Final Office Action dated Mar. 27, 2009 from corresponding U.S. Appl. No. 11/225,265.
Non Final Office Action dated Nov. 1, 2007 from corresponding U.S. Appl. No. 11/223,269.
Non Final Office Action dated Oct. 12, 2010 from corresponding U.S. Appl. No. 11/223,269.
Non Final Office Action dated Oct. 15, 2002 from corresponding U.S. Appl. No. 09/748,793.
Office Action dated Apr. 26, 2007 from corresponding European Application No. 06008833.3.
Office Action dated Aug. 2, 2010 from corresponding Japanese Application No. 2006-224749.
Office Action dated Aug. 2, 2010 from corresponding Japanese Application No. 2006-224750.
Office Action dated Feb. 16, 2006 from corresponding Japanese Application No. 2002-553108.
Office Action dated Feb. 3, 2010 from corresponding Japanese Application No. 2006-224749.
Office Action dated Feb. 3, 2010 from corresponding Japanese Application No. 2006-224750.
Office Action dated Jan. 26, 2007 from corresponding Japanese Application No. 2002-553108.
Office Action dated Jul. 29, 2009 from corresponding Japanese Application No. 2006-224749.
Office Action dated Jul. 29, 2009 from corresponding Japanese Application No. 2006-224750.
Office Action dated Jun. 18, 2009 from corresponding European Application No. 06008833.3.
Office Action dated Jun. 29, 2007 from corresponding European Application No. 06008832.5.
Yost et al, "Tandem Quadrupole Mass Spectrometry", John Wiley & Sons, 1983, pp. 175-195, Ch. 8.
Huang et al, "Characterization of Cyclodextrins Using Ion-evaporation Atmospheric-pressure Ionization Tandem Mass Spectrometry", Rapid Communications in Mass Spectrometry, 1990, pp. 467-471, vol. 4, No. 11.
Morris et al, "A Novel Geometry Mass Spectrometer, the Q-TOF, for Low-Femtomole/Attomole-Range Biopolymer Sequencing", Journal of Protein Chemistry, 1997, pp. 469-479, vol. 16, No. 5.
Morris et al, "High Sensitivity Collisionally-activated Decomposition Tandem Mass Spectrometry on a Novel Quadrupole/Orthogonal-acceleration Time-of-flight Mass Spectrometer", Rapid Communications in Mass Spectrometry, 1996, pp. 889-896, vol. 10.
Borchers et al, "Preliminary comparison of precursor scans and liquid chromatography—tandem mass spectrometry on a hybrid quadrupole time-of-flight mas spectrometer", Journal of Chromatography, 1999, pp. 119-130, vol. 854.
Charlwood et al, "Structural Characterisation of N-Linked Glycan Mixtures by Precursor Ion Scanning and Tandem Mass Spectrometric Analysis", Rapid Communications in Mass Spectrometry, 1999, pp. 1522-1530, vol. 13.
Hopfgartner et al, "Exact Mass Measurement of Product Ions for the Structural Elucidation of Drug Metabolites with a Tandem Quadrupole Orthogonal-Acceleration Time-of-Flight Mass Spectrometer", Journal of American Society for Mass Spectrometry, 1999, pp. 1305-1314, vol. 10.
Gulcicek et al, "Structural Elucidation in the Millisecond Time Frame Using Fast In-Source CID API Time-of-Flight MS", ASMS Conference 1998 Book of Abstracts, pp. 891.
Srinivas et al., "Proteomics in Early Detection of Cancer", American Association for Clinical Chemistry, vol. 47, No. 10, pp. 1901-1911, 2001.
Rosty et al., "Identification of Hepatocarcinoma-Intestine-Pancreas/Pancreatitis-Associated Protein I as a Biomaker for Pancreatic Ductal Adenocarcinoma by Protein Biochip Technology", American Association of Cancer Research, vol. 62, No. 2, pp. 1868-1875, 2002.
Willis, "Diagnosing Newborns", Modern Drug Discovery, vol. 5, No. 4, pp. 28-33, Apr. 2002.
Kang H D et al. "Radical detection in a methane plasma", J. Vac. Sci. Technol. A vol. 21, No. 6, Nov./Dec. 2003 pp. 1978-1980, XP007900816.
Preuss, R. et al. "Quantitative analysis of multicomponent mass spectra", AIP Conference Proceedings AIP USA, No. 617, 2002, pp. 155-162, XP007900817.
Hellerstein, M. K. et al. "Mass isotopomer distribution analysis at eight years: theoretical, analytic and experimental considerations", American Physiology:, vol. 276, No. 39, 1999, pp. E1146-E1170, XP002978087.
Bylund, D. et al. "Chromatographic alignment by warping and dynamic programming as a pre-processing tool for PARAFAC modeling of liquid chromatography—mass spectrometry data", J. of Chromatography A, 961, No. 2, Jul. 5, 2002, pp. 237-244, XP004370624.
Jain, A. K. et al. "Statistical Pattern Recognition: A Review", IEEE Transactions on Pattern Analysis and Machine Intelligence, IEEE Service Center, Los Alamitos, CA US, vol. 22, No. 1, Jan. 2000, pp. 4-37, XP000936788, ISSN: 0162-8828, pp. 29-31.

(56) References Cited

OTHER PUBLICATIONS

Bateman et al., "A Combined Magnetic Sector-Time-of-flight Mass Spectrometer for Structural Determination Studies by Tandem Mass Spectrometry", Rapid Communications in Mass Spectrometry, vol. 9, 1227-1233 (1995).

David K. Crockett, "Automated Screening of Metabolic Disorders Using Pattern Recognition of GC-MS Full Scan Spectra From Urine Organic Acids", Department of Medical Informatics, University of Utah, Aug. 2002.

Mariner API-TOF Workstation User Guidelines, 1999.

Quattro II User Guidelines from micromass, 1996.

Sensar Larson Davis, "Jaguar Electrospray Time-of-Flight Mass Detectors", www.lardav.com, 1997.

Vreeken et al., "Selective analysis of the herbicides glyphosate and aminomethylphosphonic acid in water by on-line solid-phase extraction-high-performance liquid chromatography-electrospray ionization mass spectrometry", Journal of Chromatography A, 794 (1998), pp. 187-199.

Wysocki et al., "Surface-induced Dissociation in Tandem Quadrupole Mass Spectrometers: A Comparison of Three Designs", J Am Soc Mass Spectrom 1992, 3, pp. 27-32.

\* cited by examiner

Figure 3

Human protein database:
    60,884 sequence entries

Fragment ion masses used for analysis:
    710.385
    753.435
    807.374
    886.402
    904.451
    1001.564

---

Bradykinin RPPGFSPFR MH+ 1060.5676
at 10 PPM, 144 tryptic peptides match
13 matches using fragment ion constraint:

ACISEILPSK
GVRYSFGFK
RANLISQCR
RCGLPSSGKR
RDITLEASR
RERETLEK
RLTEEERK
RLVEVDSSR
RNLLDHHR
RPHAAQPGAR
RPPGFSPFR   **
RPQTATASTK
RRPSAYQAL

---

ASHLGLAR MH+ 824.4739
at 10 PPM, 57 tryptic peptides match
12 matches using fragment ion constraint:

ACYIKVK
ADPLPRR
AFVAFAAK
AFVFGRK
AHAEIRK
AHEAKIR
ALEAHKR
ALQFFAK
AMAIYKK
APDPRLR
ASHLGLAR   **
AVAGHLTR

Figure 4C

METHOD OF MASS SPECTROMETRY FOR IDENTIFYING POLYPEPTIDES

This application is a continuation of U.S. application Ser. No. 09/748,783, filed Dec. 26, 2000 now abandoned, which is incorporated herein by reference.

SEQUENCE LISTING

The instant application contains a Sequence Listing which has been submitted in ASCII format via EFS-Web and is hereby incorporated by reference in its entirely. Said ASCII copy, created on Aug. 20, 2013, is named 04995700.txt and is 5,765 bytes in size.

BACKGROUND OF THE INVENTION

This invention relates generally to proteome analysis and, more specifically, to methods of identifying and/or quantifying a protein or proteins that is contained in a mixture of proteins.

The classical biochemical approach to study biological processes has been based on the purification to homogeneity by sequential fractionation and assay cycles of the specific activities that constitute a process, the detailed structural, functional and regulatory analysis of each isolated component, and the reconstitution of the process from the isolated components. The Human Genome Project and other genome sequencing programs are turning out in rapid succession the complete genome sequences of specific species and, thus, in principle the amino acid sequence of every protein potentially encoded by that species. It is to be expected that this information resource unprecedented in the history of biology will enhance traditional research methods and catalyze progress in fundamentally different research paradigms, one of which is Proteomics.

Efforts to sequence the entire human genome along with the genomes of a number of other species have been extraordinarily successful. The genomes of 46 microbial species (TIGR Microbial Database; www.tigr.org) have been completed and the genomes of over one hundred twenty other microbial species are in the process of being sequenced. Additionally, the more complex genomes of eukaryotes, in particular those of the genetically well characterized unicellular organism *Saccharomyces cerevisiae* and the multicellular species *Caenorhabditis elegans* and *Drosophila melanogaster* have been sequenced completely. Furthermore, "draft sequence" of the rice genome has been published, and completion of the human and *Arabidopsis* genomes are imminent. Even in the absence of complete genomic sequences, rich DNA sequence databases have been made publicly available, including those containing over 2.1 million human and over 1.2 million murine expressed sequence tags (ESTs).

ESTs are stretches of approximately 300 to 500 contiguous nucleotides representing partial gene sequences that are being generated by systematic single pass sequencing of the clones in cDNA libraries. On the timescale of most biological processes, with the notable exception of evolution, the genomic DNA sequence can be viewed as static, and a genomic sequence database therefore represents an information resource akin to a library. Intensive efforts are underway to assign "function" to individual sequences in sequence databases. This is attempted by the computational analysis of linear sequence motifs or higher order structural motifs that indicate a statistically significant similarity of a sequence to a family of sequences with known function, or by other means such as comparison of homologous protein functions across species. Other methods have also been used to determine function of individual sequences, including experimental methods such as gene knockouts and suppression of gene expression using antisense nucleotide technology, which can be time consuming and in some cases still insufficient to allow assignment of a biological function to a polypeptide encoded by the sequence.

The proteome has been defined as the protein complement expressed by a genome. This somewhat restrictive definition implies a static nature of the proteome. In reality the proteome is highly dynamic since the types of expressed proteins, their abundance, state of modification, and subcellular locations are dependent on the physiological state of the cell or tissue. Therefore, the proteome can reflect a cellular state or the external conditions encountered by a cell, and proteome analysis can be viewed as a genome-wide assay to differentiate and study cellular states and to determine the molecular mechanisms that control them. Considering that the proteome of a differentiated cell is estimated to consist of thousands to tens of thousands of different types of proteins, with an estimated dynamic range of expression of at least 5 orders of magnitude, the prospects for proteome analysis appear daunting. However, the availability of DNA databases listing the sequence of every potentially expressed protein combined with rapid advances in technologies capable of identifying the proteins that are actually expressed now make proteomics a realistic proposition. Mass spectrometry is one of the essential legs on which current proteomics technology stands.

Quantitative proteomics is the systematic analysis of all proteins expressed by a cell or tissue with respect to their quantity and identity. The proteins expressed in a cell, tissue, biological fluid or portein complex at a given time precisely defines the state of the cell or tissue at that time. The quantitative and qualitative differences between protein profiles of the same cell type in different states can be used to understand the transitions between respective states. Traditionally, proteome analysis was performed using a combination of high resolution gel electrophoresis, in particular two-dimensional gel electrophoresis, to separate proteins and mass spectrometry to identify proteins. This approach is sequential and tedious, but more importantly is fundamentaly limited in that biologically important classes of proteins are essentially undetectable.

Thus, there exists a need for rapid, efficient, and cost effective methods proteome analysis. The present invention satisfies this need and provides related advantages as well.

SUMMARY OF THE INVENTION

The invention provides methods for identifying polypeptides. The method can include the steps of simultaneously determining the mass of a subset of parent polypeptides from a population of polypeptides and the mass of fragments of the subset of parent polypeptides; comparing the determined masses to an annotated polypeptide index; and identifying one or more polypeptides of the annotated polypeptide index having the determined masses. The method can further include the steps of determining one or more additional characteristics associated with one or more of the parent polypeptides; comparing the determined characteristics to the annotated polypeptide index; and optionally repeating the steps one or more times, wherein a set of characteristics is determined that identifies a parent polypeptide as a single polypeptide in the annotated polypeptide index. The method can additionally include the step of quantitating the amount of the identified polypeptide in a sample containing the polypeptide.

BRIEF DESCRIPTION OF THE DRAWINGS

FIG. 2A shows the selection of a parent ion (in Q1), which is fragmented in a collision cell (Q2). A mass spectrum of the fragments is determined (in Q3). FIG. 2B shows that, instead of selecting a single parent ion, multiple parent ions (indicated in "Source region") are concurrently fragmented in the post-ionization region or collision cell. The fragment ions are then analyzed in a Q1 or other mass analyzer, resulting in a mass spectrum consisting of fragment ions from multiple parent ions.

FIG. 3 shows the steps of a method for comparing and quantitating two polypeptide populations using a polypeptide identification index of Annotated Peptide Tags.

FIG. 4 shows identification of a polypeptide using mass spectrometry (MS). FIG. 4C shows a list of 13 and 12 possible polypeptide identifications for P1 and P2, respectively. FIG. 4A discloses SEQ ID NOs: 1 and 2, respectively, in order of appearance from top to bottom; and FIG. 4C discloses SEQ ID NOs: 2,3-12,2,13-14,1-15-24,1, and 25, respectively, in order of appearance from top to bottom.

DETAILED DESCRIPTION OF THE INVENTION

Figure 1:
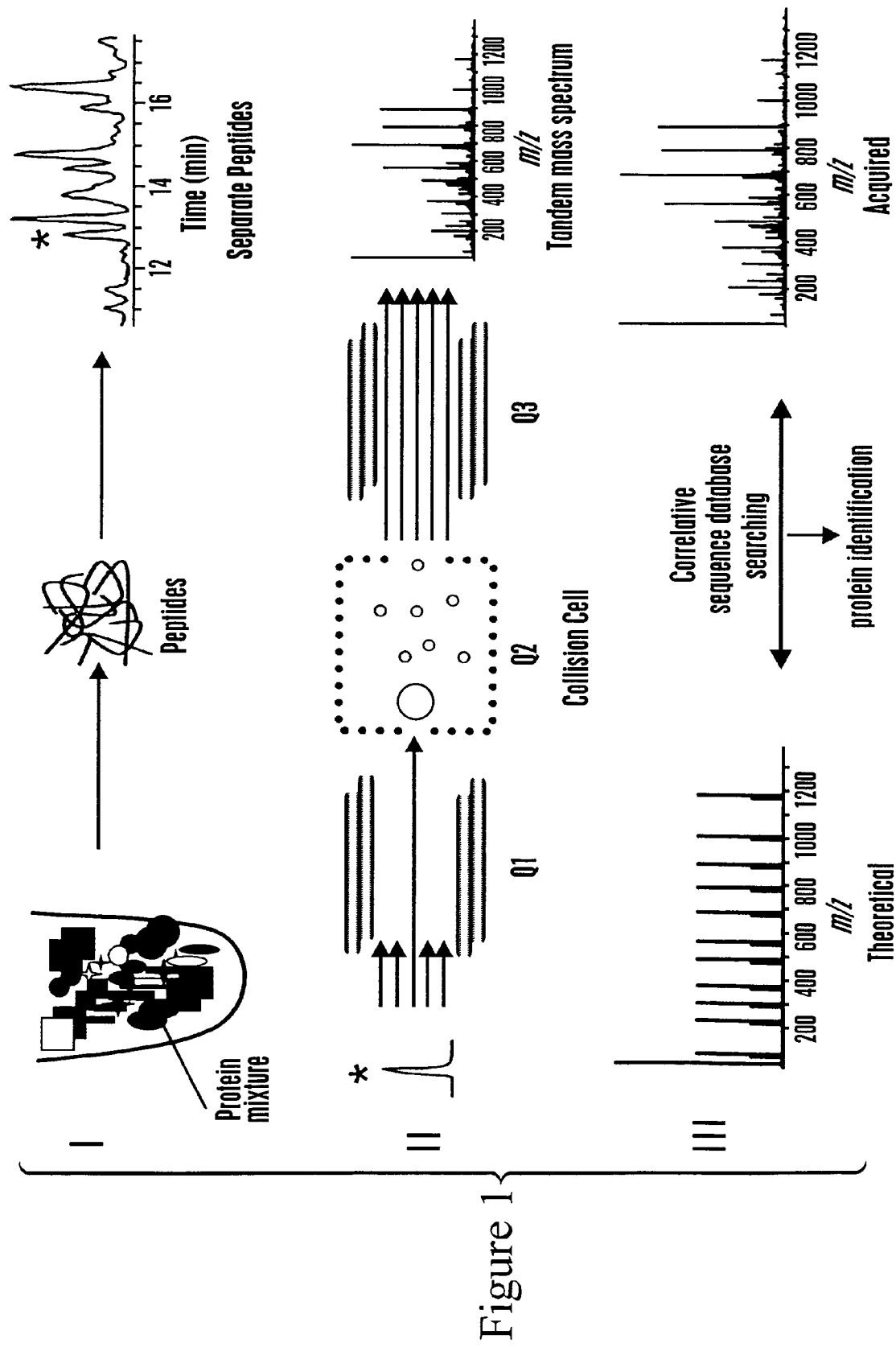
FIG. 1 shows a schematic diagram of a protein identification strategy based on mass spectrometry (MS) and tandem mass spectrometry (MS/MS) measurements.

The invention provides methods for identifying a polypeptide from a population of polypeptides by determining characteristics associated with a polypeptide, or a peptide fragment thereof, comparing the determined characteristics to a polypeptide identification index, and identifying one or more polypeptides in the polypeptide identification index having the same characteristics. The methods of the invention are applicable to proteome analysis and allow rapid and efficient identification of one or more polypeptides in a complex sample. The methods are based on generating a polypeptide identification index, which is a database of characteristics associated with a polypeptide. The polypeptide identification index can be used for comparison of characteristics determined to be associated with a polypeptide from a sample for identification of the polypeptide. Furthermore, the methods can be applied not only to identify a polypeptide but also to quantitate the amount of specific proteins in the sample.

The methods of the invention for identifying a polypeptide are applicable to performing quantitative proteome analysis, or comparisons between polypeptide populations that involve both the identification and quantitation of sample polypeptides. Such a quantitative analysis can be conveniently performed in two separate stages, if desired. As a first step, a reference polypeptide index can be generated representative of the samples to be tested, for example, from a species, cell type or tissue type under investigation, as described herein. The second step is the comparison of characteristics associated with an unknown polypeptide with the reference polypeptide index or indices previously generated. A reference polypeptide index is a database of polypeptide identification codes representing the polypeptides of a particular sample, such as a cell, subcellular fraction, tissue, organ or organism. A polypeptide identification index can be generated that is representative of any number of polypeptides in a sample, including essentially all of the polypeptides potentially expressed in a sample. Accordingly, the methods of the invention advantageously allow the determination of polypeptides in a sample that correlates with or defines a particular physiological state of the sample, for example, a disease state. Moreover, once a polypeptide identification index has been generated, the index can be used repeatedly to identify one or more polypeptides in a sample, for example, a sample from an individual potentially having a disease.

For quantitation of a polypeptide in a sample, a polypeptide is compared to a chemically identical molecule that is isotopically labeled, for example, with $^{13}C$ for $^{12}C$, deuterium for hydrogen, or $^{18}O$ for $^{16}O$. Any number of differential isotopes can be incorporated so long as there is a sufficient difference in mass to be distinguished by MS, as disclosed herein. Because the molecules are chemically identical except for the isotopic difference, the molecules behave physicochemically the same. Furthermore, if desired, more than two samples can be compared if a sufficient number of isotopic labels (e.g., d0, d4, d8, d12) are available such that the multiple samples can be compared and distinguished by MS. Quantitation is based on stable isotope dilution. One method to quantitate a sample is to spike a sample with an internal standard that is chemically identical but isotopically different. A standard curve can be generated with dilution of isotope to extrapolate the quantity of molecule in a sample. In such a case, the molecule to be spiked must be identical and therefore the molecules in the sample must be known.

Another convenient method for quantitating polypeptides in a sample is to use a reagent such as ICAT™ (Gygi et al., *Nature Biotechnol.* 17:994-999 (1999); WO 00/11208). An ICAT™ type reagent, which is described in more detail below, contains an affinity tag, a linker moiety in which one or more stable isotopes can be incorporated, and a reactive group that can covalently couple to an amino acid side chain in a polypeptide such as a cysteine. For quantitation using an ICAT™ type reagent, parallel samples are treated with different isotopic versions of the ICAT™ type reagent. A sample can be labeled and compared to a parallel labeled sample, for example, to normalize to a reference or control sample for quantitation. The use of an ICAT™ type reagent to identify and quantitate polypeptides in a sample is illustrated in FIG. 3. Because the peptides labeled with different isotopic versions of the ICAT™ type reagent behave physicochemically the same, the same polypeptides in the two samples will co-purify but still be distinguishable by MS due to the isotopic differences in the ICAT™ type label. Accordingly, the relative amounts of the same polypeptides can be readily compared and quantitated (Gygi et al., supra, 1999). Every other scan can be devoted to fragmenting and then recording sequence information about an eluting peptide (MS/MS spectrum). The parent polypeptide that this peptide originated from can be identified by searching a sequence database with the recorded MS/MS spectrum. The procedure thus provides the relative quantitation and identification of the components of protein mixtures in a single analysis. Such a comparison can be useful for quantitating the expression levels of polypeptides relative to a reference sample, for example, comparing expression levels in a sample from an individual having a disease or suspected of having a disease to a sample from a healthy individual or for forensic purposes.

In addition to being useful for quantitation of polypeptides, an ICAT™ type reagent also functions as a constraint on the complexity of the system, that is, only polypeptides or fragments thereof containing the amino acid reactive with the ICAT™ type reagent will be labeled and characterized if the polypeptides are affinity isolated or compared side-by-side with a differentially isotopically labeled sample (Gygi et al., supra, 1999). Accordingly, the use of an ICAT™ type reagent can provide a reduction in complexity of the sample. Furthermore, the ability of a polypeptide or fragment thereof to be labeled with an ICAT™ type reagent, that is, whether the peptide contains the reactive amino acid, is a characteristic associated with the polypeptide useful for identifying the polypeptide in combination with additional characteristics.

An additional advantage of the use of an ICAT™ type reagent is that the identity of polypeptides in a sample need not be known prior to analysis. As described above, isotopic dilution, where an internal standard is spiked into a sample, requires that a chemically identical molecule that is differentially isotopically labeled be spiked into the sample and, therefore, requires that a polypetpide or fragment thereof to be quantitated is known so that a chemically identical isotopically labeled molecule be added. With an ICAT™ type reagent, no prior knowledge of the exact polypeptides or fragments need be known. Furthermore, there is no need to synthesize a variety of isotopically labeled molecules for characterizing a variety of polypeptides in a sample.

In addition to using a labeling reagent such as an ICAT™ type reagent that incorporates an affinity label, other labeling reagents can be used to differentially isotopically label two different samples containing polypeptides. For example, two chemically identical reagents containing different isotopes can be used to covalently modify two polypeptide samples, where the reagents do not contain an affinity tag. Accordingly, instead of using an affinity isolation step associated with an ICAT™ type tag, other isolation steps, if desired, can be used. Nevertheless, the differentially isotopically labeled polypeptide samples can be compared for quantitative analysis. For example, methylation of polypeptides via esterification with methanol containing d0 (no deuterium) versus d3 (three deuteriums) can be used to differentially isotopically label two polypeptide samples. Similarly, any of the well known methods for modifying side chain amino acids in polypeptides can analogously be used with differentially labeled isotopes such as deuterium for hydrogen, $C^{13}$ for $C^{12}$, $O^{18}$ for $O^{16}$ (see, for example, Glazer et al., *Laboratory Techniques in Biochemistry and Molecular Biology: Chemical Modification of Proteins*, Chapter 3, pp. 68-120, Elsevier Biomedical Press, New York (1975); Pierce Catalog (1994), Pierce, Rockford Ill.). Any number of the differential isotopes can be incorporated so long as parallel labeled polypeptides contain a sufficient mass distinction to be detected by MS. In addition to chemical modification of a polypeptide, as described above, two polypeptide samples can be digested with a protease such as trypsin or the like in the presence of $O^{16}$- versus $O^{18}$-labeled $H_2O$. Since the protease cleavage reaction results in the addition of water to the cleaved peptides, cleavage in the presence of isotopically differentially labeled $H_2O$ can be used to incorporate differential labels into separate polypeptide samples. It is understood that any method useful for incorporating an isotopic label to differentially label two polypeptide samples can be used in methods of the invention, particularly for quantitative methods, so long as the samples to be compared are treated in a chemically similar fashion such that the resulting labeled polypeptides essentially differ only by the differential isotopic label.

Still another method to quantitate a sample is to incubate a sample under conditions that allow metabolic incorporation of isotopes into two samples for comparison by incubating a sample in the presence of an isotope or incubating in media that results in depletion of a naturally occurring isotope (see, for example, Oda et al., *Proc. Natl. Acad. Sci. USA* 96:6591-6596 (1999)). Such a method is particularly useful for a sample that is conveniently cultured, for example, a microbial sample or a primary culture of cells obtained from an individual. Accordingly, both in vitro and in vivo methods can be used to differentially isotopically label two samples for comparison and/or quantitation.

The methods of the invention are based on determining characteristics of a polypeptide that allow identification of the polypeptide based on the determined physicochemical characteristics. The collection of physicochemical characteristics that can function to identify a polypeptide is essentially a "bar code" for the polypeptide, that is, a collection of characteristics sufficient to uniquely identify a polypeptide based on correlating the characteristics with a reference database that functions as a polypeptide identification index. The methods are particularly advantageous for rapid and efficient analysis of complex samples containing many different polypeptides, which would be time consuming and inefficient using other methods. The methods of the invention can thus be applied to analyze complex samples containing numerous different polypeptides and are particularly useful in proteomics applications. Accordingly, the methods of the invention can be advantageously used to identify polypeptides of the proteome. Since the proteome reflects polypeptide expression and post-translational modifications correlated with the metabolic state of the cell, the methods can also be used in diagnostic applications to determine normal or aberrant polypeptide expression associated with a disease. Accordingly, the methods of the invention can be used in clinical applications to diagnose a disease or condition.

The methods of the invention advantageously use constraining parameters that allow the identification of a polypeptide from a complex mixture of different polypeptides. The constraints can be used to simplify the identification of polypeptides. A constraint can be, for example, the inclusion of one or more additional characteristics associated with a polypeptide, the identification of a subset of polypeptides from a complex mixture, or any type of constraint that can be used to simplify the analysis of a complex mixture of polypeptides. The methods of the invention thus provide more efficient identification of polypeptides in a complex mixture, including large numbers of polypeptides, which is particularly useful for proteome analysis.

The generation and use of a polypeptide identification index provide several advantages. First, the methods can be used with selective isolation of polypeptide fragments containing specific structural features, which can be exploited by tagging with specific chemical reagents. The affinity selection of "tagged" fragments simplifies the polypeptide mixture, rendering it compatible with highly denaturing/solubilizing conditions that can be used for protein isolation and handling. The selective isolation of fragments also constrains database searching. For example, selective cysteine tagging, as disclosed herein, reduces the complexity of the peptide mixture by approximately 10-fold.

A second advantage of the invention methods is that they can be readily used in a variety of laboratory settings. For example, mass measurements are absolute and chromatographic parameters can be easily standardized. Therefore, a polypeptide identification index determined by methods of the invention is easily transferable between laboratories, and data generated by different laboratories can be easily compared with a polypeptide identification index generated under similar conditions. This advantage can be further exploited by making the method accessible via a network, for example, through the construction of a Web-based search tool. A third advantage is that the methods can be performed with a single stage mass analysis, which is fast, simple and sensitive. A fourth advantage is that the methods can be used to accurately measure the ratio of each polypeptide present in a complex polypeptide sample, provided that the samples have been modified with a stable isotope label. Finally, the methods have an essentially unlimited sample capacity, assuring the possibility of analyzing polypeptides of very low abundance, and have a high peak capacity, allowing for the analysis of very complex samples.

Figure 2:
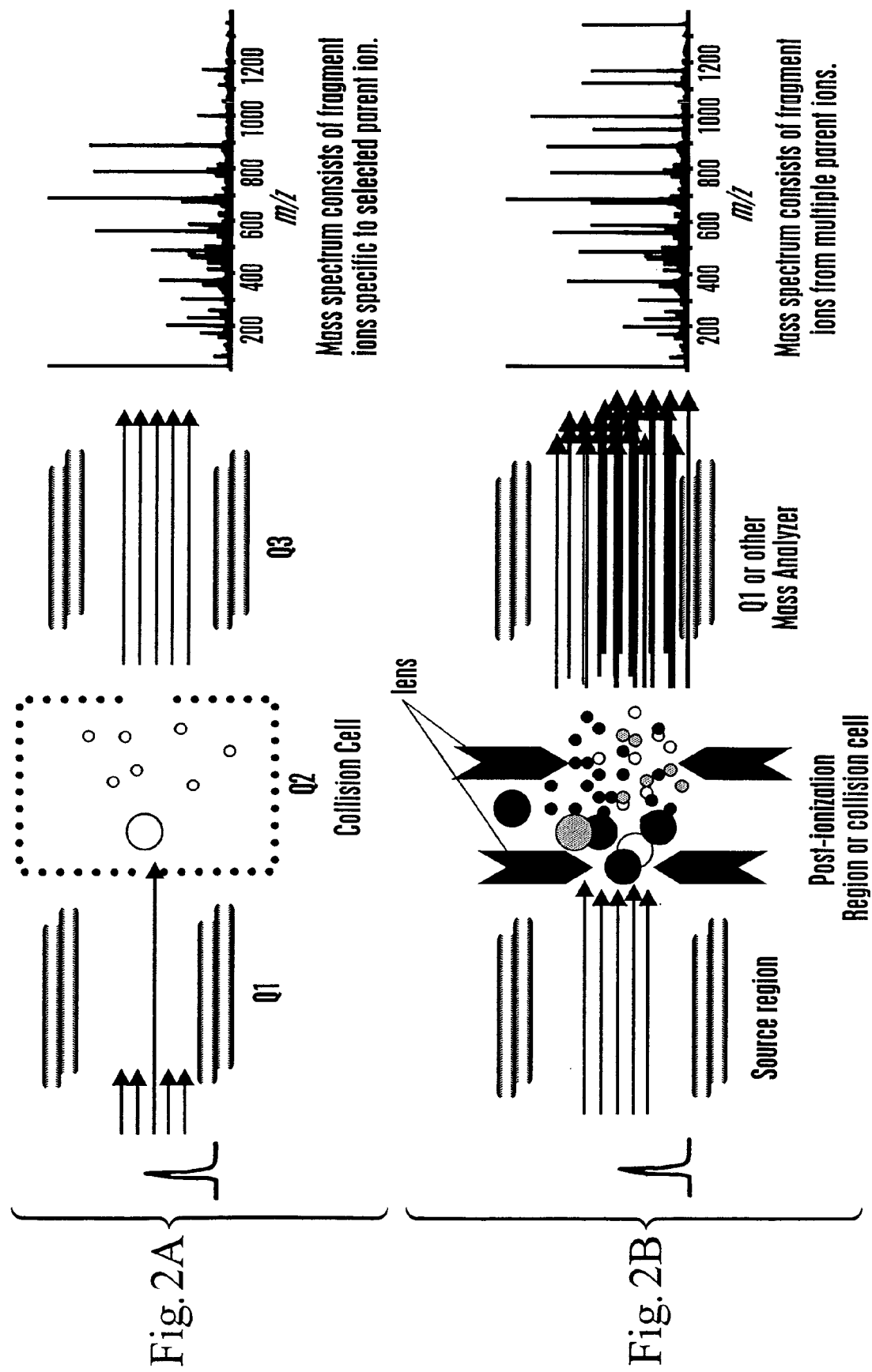
FIG. 2 shows two different methods to generate fragment ion selected peptide ions that are diagnostic for the identification of the parent ion.

As disclosed herein, in addition to isolating individual parent ions prior to fragmentation, multiple ions can be fragmented in parallel without single ion selection (see FIG. 2). Accordingly, a key advantage of such a method is that the parameters can be easily determined in parallel for multiple polypeptides rather than separately for each peptide as is the case in protein identification by MS/MS.

In one embodiment of the invention, a polypeptide identification index is generated by determining characteristics associated with a polypeptide, in particular, fragment ion mass measurements by MS/MS generated with or without parent ion selection (FIG. 2) and optionally including chromatographic steps. These mass determinations are not required to be at high accuracy. The accurate mass can be calculated, if desired, and compiled into an index with other characteristics associated with a particular polypeptide. A sufficient number of characteristics are determined to allow identification of a polypeptide in the index. The methods can optionally and advantageously be used with quantitation to provide additional information on the physiological state of a sample. However, in the case of simpler systems, for example, microbial or viral genomes or specimens from an individual containing a smaller number of polypeptides such as spinal fluid, the complexity of polypeptides in a sample can be sufficiently small enough that qualitative analysis of the polypeptides in a sample is sufficient for particular applications. As such, if a qualitative determination of the expression of a polypeptide in a sample is sufficient to correlate with a particular condition, for example, a disease condition, then the methods of the invention can be applied to a qualitative identification of a polypeptide in a sample.

For example, as shown in FIG. 2, an invention method can be performed in the absence of single ion selection or in the absence of ion selection in a source region. The regions designated, for example, as $Q_1$, $Q_2$, $Q_3$ and the like, refers to quadrupoles. These are physical means to separate a selected ion based on m/z. However, it is understood that any appropriate methods suitable for separating selected ions, in addition to the use of quadrupoles, can be used in methods of the invention.

As used herein, the term "characteristic" when used in reference to a polypeptide refers to a physicochemical property of a polypeptide. Physicochemical properties include physicochemical properties of a parent polypeptide such as molecular mass, amino acid composition, pI and the like, as well as physicochemical properties of a fragment of a polypeptide, including fragment ions, which can be correlated with a polypeptide and are thus considered to be characteristics associated with a parent polypeptide. Physicochemical properties of a polypeptide also include measurable behaviors of a polypeptide that result from its particular physicochemical properties. For example, physicochemical properties include the order of elution on specific chromatographic media under defined conditions, and the position to which a polypeptide migrates in a polyacrylamide gel under defined conditions. The characteristics can be determined empirically or can be predicted based on known information about the polypeptide, for example, sequence information.

As used herein, the term "characteristics associated with a polypeptide" refers to physicochemical properties of a polypeptide and/or any fragment of the polypeptide. As such, the characteristics associated with a polypeptide include specific characteristics of a parent polypeptide as well as characteristics of a fragment of the parent polypeptide which, because the fragment can be related to the polypeptide, are considered to be characteristics associated with the parent polypeptide. Such characteristics can be used to identify a polypeptide, for example, by comparison with a polypeptide identification index.

As used herein, the term "polypeptide" refers to a peptide or polypeptide of two or more amino acids. A polypeptide can also be modified by naturally occurring modifications such as post-translational modifications, including phosphorylation, lipidation, prenylation, sulfation, hydroxylation, acetylation, addition of carbohydrate, addition of prosthetic groups or cofactors, formation of disulfide bonds, proteolysis, assembly into macromolecular complexes, and the like.

A modification of a polypeptide, particularly ligand polypeptides, can also include non-naturally occurring derivatives, analogues and functional mimetics thereof generated by chemical synthesis, provided that such polypeptide modification displays a similar functional activity compared to the parent polypeptide. For example, derivatives can include chemical modifications of the polypeptide such as alkylation, acylation, carbamylation, iodination, or any modification that derivatizes the polypeptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those polypeptides which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by peptide bonds.

A particularly useful polypeptide derivative includes modification of sulfhydryl groups, for example, the modification of sulfhydryl groups to attach affinity reagents such as an ICAT™ type reagent. A particularly useful modification of a polypeptide includes modification of polypeptides in a sample with a moiety having a stable isotope. For example, two different polypeptide samples can be separately labeled with moieties that are isotopically distinct, and such differentially labeled samples can be compared. Modification of polypeptides with stable isotopes is particularly useful for quantitating the relative amount of individual polypeptides in a sample.

As used herein, a "fragment" refers to any truncated form, either carboxy-terminal, amino-terminal, or both, of a parent polypeptide. Accordingly, a deletion of a single amino acid from the carboxy- or amino-terminus is considered a fragment of a parent polypeptide. A fragment generally refers to a deletion of amino acids at the N- and/or C-terminus but also includes modifications where a side chain is removed but the peptide bond remains. A fragment includes a truncated polypeptide that is generated, for example, by polypeptide cleavage using a chemical reagent, enzyme, or energy input.

A fragment can result from a sequence-specific or sequence independent cleavage event. Examples of reagents commonly used for cleaving polypeptides include enzymes, for example, proteases, such as thrombin, trypsin, chymotrypsin and the like, and chemicals, such as cyanogen bromide, acid, base, and o-iodobenzoic acid, as disclosed herein. A fragment can also be generated by a mass spectrometry method. Furthermore, a fragment can also result from multiple cleavage events such that a truncated polypeptide resulting from one cleavage event can be further truncated by additional cleavage events.

As used herein, the term "polypeptide identification index" refers to a collection of characteristics associated with a polypeptide sufficient to identify and distinguish other polypeptides in the index. A polypeptide identification index is therefore a collection of polypeptide identification codes for identifying a polypeptide based on characteristics of the polypeptide or a fragment thereof. A polypeptide identification index can be based on deduced characteristics associated with a polypeptide, for example, characteristics predicted based on sequence information such as genomic sequence, cDNA sequence, or EST databases. A polypeptide identification index can also be based on empirically determined characteristics, or a combination of deduced and empirically determined characteristics. An "annotated polypeptide (AP) index" refers to an index comprising at least one empirically determined characteristic for each of the polypeptides in the index, which can be determined, for example, by the methods disclosed herein. If desired, an AP index can be based on entirely empirically determined characteristics or a combination of deduced and empirically determined characteristics. The use of an annotated polypeptide index is particularly useful for identifying polypeptides modified by post-translational modifications, which can have characteristics unpredictable based on deduction from a sequence database alone.

A "polypeptide identification subindex" refers to a subset of a polypeptide identification index that contains less than all of the polypeptide identification codes of the polypeptide identification index. A subindex can contain, for example, five polypeptide identification codes from a polypeptide identification index of ten polypeptide identification codes, which is a subset of the entire index. Identification of a subindex can be useful, for example, for reducing the complexity of a search of a polypeptide identification index, similar to the reduction in complexity that can be applied to a polypeptide sample by the fractionation methods disclosed herein. Accordingly, a search of a subindex can be advantageous in requiring less computational time than required to search an entire index.

As used herein, the term "identification code" refers to a set of characteristics associated with a polypeptide that is sufficient to determine the identity of the polypeptide and distinguish the polypeptide from other polypeptides in a polypeptide identification index. An identification code is essentially an annotated peptide tag, or "bar code," that can be used to identify a polypeptide.

The invention provides a method for identifying a polypeptide. The method includes the steps of determining two or more characteristics associated with a polypeptide or fragment thereof, one of the characteristics being the mass of a fragment of the polypeptide, wherein the fragment mass is determined by mass spectrometry; comparing the characteristics associated with the polypeptide to a polypeptide identification index such as an annotated polypeptide index; and identifying one or more polypeptides in the polypeptide identification index having the determined characteristics. The fragment can be determined at an accuracy in ppm of greater than 1 part per million (ppm) or at even lower accuracy (higher ppm). The method can further include determining one or more additional characteristics associated with the polypeptide and comparing the characteristics determined in each of the steps to the polypeptide identification index. Optionally, the steps of determining one or more additional characteristics associated with the polypeptide and comparing the characteristics determined in each step to the polypeptide identification index can be repeated one or more times, wherein a set of characteristics is determined that identifies a single polypeptide in the polypeptide identification index. The method can further include quantitating the amount of polypeptide in a sample. Furthermore, the methods can be used to measure the relative abundance in two or more different populations of polypeptides, that is, polypeptide mixtures, for example, populations of polypeptides in different samples.

The methods of the invention for identifying a polypeptide include determining characteristics associated with the polypeptide, or a fragment of the polypeptide. Characteristics associated with a polypeptide that are useful for identifying a polypeptide are those characteristics that can be reproducibly determined. Physicochemical properties of a polypeptide or fragment include, for example, atomic mass, amino acid composition, partial amino acid sequence, apparent molecular weight, pI, and order of elution on specific chromatographic media under defined conditions. Such characteristics determined to be associated with a polypeptide are used for the identification of the polypeptide. Methods for determining characteristics associated with a polypeptide are described in more detail below.

One of the characteristics particularly useful in methods of the invention is the mass of a polypeptide or a fragment or fragments thereof. A fragment of a polypeptide can be generated prior to or during the process of mass determination by mass spectrometry. A polypeptide fragment mass can therefore be the mass of a fragment of a polypeptide generated during polypeptide sample preparation, or can be the mass of fragment generated by a polypeptide cleavage that occurred during mass spectrometry.

In the methods of the invention, the mass of a polypeptide fragment is determined by mass spectrometry, and can advantageously be determined in the absence of ion selection for producing fragment ions. The methods of the invention allow the identification of a polypeptide without the need for sequencing the polypeptide or fragment thereof. A polypeptide fragment mass can be determined using a variety of mass spectrometry methods known in the art, as described herein.

A variety of mass spectrometry systems can be employed in the methods of the invention for identifying a polypeptide. Mass analyzers with high mass accuracy, high sensitivity and high resolution include, but are not limited to, matrix-assisted laser desorption time-of-flight (MALDI-TOF) mass spectrometers, ESI-TOF mass spectrometers and Fourier transform ion cyclotron mass analyzers (FT-ICR-MS). Other modes of MS include an electrospray process with MS and ion trap. In ion trap MS, fragments are ionized by electrospray or MALDI and then put into an ion trap. Trapped ions can then be separately analyzed by MS upon selective release from the ion trap. Fragments can also be generated in the ion trap and analyzed. The ICAT™ type reagent labeled polypeptides that can be used in the methods of the invention can be analyzed, for example, by single stage mass spectrometry with a MALDI-TOF or ESI-TOF system.

If desired, different MS analysis can be applied for generating a polypeptide identification index than for determining characteristics of an unknown polypeptide. For example, LC- MS/MS can be used for collecting data for the identification index and LC-ESI-TOF can be used for measurement of characteristics of an unknown polypeptide. It is understood that any MS methods and any combination of MS methods can be used so long as the samples are treated in a substantially similar manner and so long as the MS methods are compatible for comparison of masses determined by the different methods.

The methods of the invention can involve a polypeptide separation step followed by a mass analysis step. Polypeptide separation and mass analysis steps can be performed independently or can be coupled in an "on line" analysis method. Various modes of polypeptide separation techniques can be coupled to a mass analyser. For example, polypeptides can be separated by chromatography using microcapillary HPLC, by solid phase extraction-capillary electrophoresis systems that can be coupled to a mass analyzer, or by gel electrophoresis methods. A specific example of a coupled polypeptide separation and mass analysis method is micro-capillary HPLC coupled to an ESI-MS/MS system that is applied with dynamic exclusion on an ion trap MS.

Different types of mass spectrometry can be used for different applications of the methods of the invention. For certain applications, such as mass determination of a polypeptide fragment for generating a polypeptide identification index, a method that provides high accuracy, such as an accuracy of less than 1 part per million. However, the methods of the invention are advantageous in that MS of lower accuracy, that is higher ppm resolution, can be conveniently used without the need for more expensive instrumentation required for higher accuracy determinations. For applications that involve high throughput analysis of a population of polypeptides, a lower accuracy mass determination can be sufficient. Lower accuracy mass determinations generally provide higher sample throughput because less time is required to make a mass determination.

The methods of the invention involving mass determinations can be conveniently performed at lower accuracy. For example, high mass accuracy instruments such as FTMS or FTICR MS can be used to determine accuracy at 0.2 ppm (Goodlett et al. et al., *Anal. Chem.* 72:1918-1924 (2000)). The use of very high mass accuracy such as 0.1 ppm acts as a constraint. However, the methods of the invention are advantageous in that several characteristics associated with a polypeptide can be determined. When combined with additional characteristics, the masses can be determined at lower accuracy, that is higher ppm. Determination of mass at lower accuracy allows the use of less expensive MS instruments which are more widely available than FTMS. The mass determinations can be determined at an accuracy in ppm of 1 part per million (ppm) or greater than 1 ppm, and can be determined at an accuracy in ppm of 2.5 ppm or greater, of about 5 ppm or greater, about 10 ppm or greater, about 50 ppm or greater, about 100 ppm or greater, about 200 ppm or greater, about 500 ppm or greater, or even about 1000 ppm or greater, sequentially each of which requires less accuracy of the MS instrument. The methods of the invention advantageously allow the use of lower accuracy MS analysis in combination with other physicochemical characteristics, as disclosed herein to identify a polypeptide in a sample. The accuracy of the MS measurement for a particular application can be readily determined by one skilled in the art, for example, depending on the complexity of the sample and/or index to be used.

The methods of the invention for identifying a polypeptide can involve determining the mass of a polypeptide fragment at an accuracy of greater than 1 part per million. Therefore, the method does not require a MS method having high accuracy. Accordingly, a lower-cost MS system can be employed in the methods of identifiying a polypeptide. The adaptation of any mass spectrometer to a high throughput format, such as 96-well plate or 384 spot plate format, or to an autoinjection system that allows unattended operation, is advantageous for increasing sample throughput.

In methods of the invention, the mass of a polypeptide or fragment thereof can be determined in the absence of ion selection for producing fragment ions. An overview of the strategy of a protein identification method is shown in FIG. 1. Polypeptides are optionally fractionated, for example, using polyacrylamide gel electrophoresis, and the polypeptides can further be fragmented into peptides. The peptides can further be optionally fractionated by chromatography. A chromatographic fraction, or bin (indicated by "*" in FIG. 1), is subjected to MS. Traditionally, an ion or dominant ions are selected in a collision cell for collision-induced dissociation (CID). Selection of a single ion is depicted in Q1 of FIG. 1. An ion is selected and then fragmented, as shown in Q3 of FIG. 1. In the absence of ion selection, instead of a single ion being selected, no selection of ions is applied but, rather, all of the ions are fragmented, leading to many peptide fragments. The peptide fragments are deconvoluted to determine which correspond to a particular parent polypeptide, and such information on the mass of a fragment of a polypeptide is a characteristic associated with the polypeptide (see FIG. 4). As shown in the bottom of FIG. 1, the fragment masses can be combined with any number of additional characteristics and compared to a protein identification index, for example, a sequence database, and the polypeptide is identified based on those determined characteristics.

A set of determined characteristics associated with a polypeptide are compared to the characteristics associated with a polypeptide in a polypeptide identification index. A polypeptide identification index is a collection of characteristics associated with individual polypeptides that uniquely identify and distinguish the polypeptides from other polypeptides annotated in the index. By comparing the set of determined characteristics associated with a polypeptide to a polypeptide identification index, one or more polypeptides in the polypeptide identification index that share the same characteristics can be identified. If more than one polypeptide is determined to have the same characteristics, additional constraints can be included, for example, the determination of one or more additional characteristics. A polypeptide identification index can be based on deduced characteristics of a polypeptide, for example, one or more characteristics deduced from genetic sequence databases, or can be determined empirically, as with the annotated peptide tag index described herein.

One exemplary method of generating an annotated peptide index is to: Harvest Proteins; Label Proteins with an Isotope Coded Affinity Tag (ICAT™) type Reagent; Fractionate Proteins by Molecular Weight; Digest Proteins to Peptides (e.g. using Trypsin); Separate Peptides by Ion Exchange; Purify each Ion Exchange Fraction by Affinity chromatography; Analyze each Affinity chromatography Fraction by LC/MS/MS (or CE/MS/MS); Identify all Expressed Proteins via Database Search of individual MS/MS Peptide Spectra; Generate a Database of Annotated Peptide Tags that constitute a unique barcode for an individual; Peptide based on measured Physicochemical properties and thus the Parent Protein of that Peptide. It is understood that the above-described method, combinations of these steps, modifications thereof, or any methods suitable to allow the determination of characteristics associated with a polypeptide can be used to generate a polypeptide identification index containing at least one empirically determined characteristic, as described herein.

The methods of the invention can further include determining one or more additional characteristics associated with the polypeptide for comparison with a polypeptide identification index. The process of determining one or more additional characteristics associated with a polypeptide followed by comparing with a polypeptide identification index can be repeated until a single polypeptide is uniquely identified from the polypeptide identification index. Accordingly, if additional constraints are applicable, they can be included to identify a polypeptide by comparison to a polypeptide identification index (see FIG. 4C).

The number of characteristics sufficient to identify of a polypeptide can be readily determined by one skilled in the art by comparing the determined set of characteristics with the polypeptide identification index. The identification of a single polypeptide in a polypeptide identification index refers to determining a set of characteristics that are sufficient to distinguish the polypeptide from another polypeptide in the polypeptide identification index. For example, if two determined characteristics match a single polypeptide in a polypeptide identification index, then the two characteristics are sufficient to identify a single polypeptide. Similarly, for a different polypeptide, three determined characteristics can be required to uniquely identify a polypeptide in the index. Accordingly, based on the characteristics determined for a polypeptide, a comparison is made to a polypeptide identification index. If a single polypeptide is identified, then a sufficient number of characteristics have been determined. If more than one polypeptide is identified, then one or more additional characteristics can be determined until a single polypeptide uniquely matches the determined characteristics, thereby allowing identification of the polypeptide. Therefore, one skilled in the art can readily determine if a sufficient number of characteristics, based on comparison to a particular polypeptide identification index, have been determined for a polypeptide to allow identification of a unique polypeptide in the polypeptide identification index.

The methods of the invention are advantageously based on the inclusion of selected constraints that allow more efficient identification of a polypeptide, particularly in complex samples containing numerous different polypeptides. The methods can also be advantageously used to identify multiple polypeptides simultaneously from a complex sample. Accordingly, rather than determining a large number of characteristics associated with different polypeptides, the methods can be performed in an iterative manner, if desired, with the inclusion of additional constraints as needed to identify a single polypeptide in a polypeptide identification index.

For example, polypeptides that are homologous generally have segments of high sequence identity. Such polypeptides can arise, for example, from polypeptides having similar function, splice variants of the same nucleic acid, and the like. Polypeptides having segments of high sequence identity can have in common several physicochemical characteristics, particularly in association with homologous fragments of the polypeptide. Polypeptides sharing a high degree of similarity can therefore have a similar or identical set of associated characteristics. For such similar polypeptides, a given set of characteristics sufficient to distinguish two dissimilar polypeptides can be insufficient for the identification of a single polypeptide in a polypeptide identification index when the polypeptides have regions of similarity. In such a case, one or more additional characteristics associated with the polypeptide can be determined, and the determination of additional characteristics can be repeated until the subject polypeptide can be distinguished from each other polypeptide in a polypeptide identification index. The methods of determining a set of characteristics associated with a polypeptide, comparing with a polypeptide identification index, and determining additional characteristics until a single polypeptide in a polypeptide identification index is identified can be applied to one or more polypeptides.

Thus, additional constraints, as needed to identify a polypeptide, can be considered. For example, if more than one polypeptide in a polypeptide identification index has a given set of characteristics, the identification of selected polypeptides of the polypeptide identification index, that is, a subset of polypeptides in the index or a subindex of the index, functions essentially as a constraint. Accordingly, a subsequent comparison to the polypeptide identification index can be made to the subindex, which can reduce the calculation time and provide a more efficient comparison, if desired. An additional constraint can then be considered, for example, an additional characteristic, and compared to the subindex, which can result in a reduction in the number of polypeptides having all of the determined characteristics. Such steps can be optionally repeated until a single polypeptide in the polypeptide identification index is identified. Such an approach is advantageous when determining the identity of multiple polypeptides simultaneously because only those characteristics sufficient to identify a polypeptide need be determined. The methods can thus readily accommodate the determination of the identity of a variety of polypeptides and the complexities associated with proteomics analysis without wasting resources on unnecessary data acquisition.

The methods of the invention for generating a polypeptide identification index involve determining, for two or more polypeptides, a set of characteristics that can be used to identify the polypeptide. A set of characteristics that uniquely identify a polypeptide in a polypeptide identification index define a polypeptide identification code or "bar code" for the polypeptide. A polypeptide identification index can contain a variety of characteristics associated with an indexed polypeptide. Polypeptide characteristics contained in a polypeptide identification index can include polypeptide mass, amino acid composition, partial amino acid composition, for example, the presence of a particular amino acid, pI, order of elution on specific chromatographic media, and one or more polypeptide fragment masses. A polypeptide identification index can additionally include amino acid sequence, references to related polypeptides, database entries or literature, as well as other information relevant to the identification of a polypeptide. The user will know what types of information are useful for a polypeptide index and can include any physicochemical property or information relating to a polypeptide. A polypeptide identification index containing a large number of identification codes for a variety of polypeptides is particularly useful for identifying polypeptides in complex samples.

The methods of the invention directed to identifying a polypeptide are based on comparing characteristics determined for a polypeptide with a polypeptide identification index. A polypeptide identification index can be a commercially or publicly available database such as GenBank (www.ncbi.nlm.nih.gov/GenBank), in which one or more characteristics of a polypeptide are predicted, for example, amino acid composition, mass of a polypeptide or fragment thereof, and the like. In addition, a polypeptide identification index can be based on empirically determined characteristics determined by the methods described herein. In addition, a polypeptide identification index can be a combination of predicted and empirically determined characteristics, for example, like the annotated polypeptide (AP) index disclosed herein, also referenced as an annotated peptide tag (APT) index.

The set of characteristics associated with a polypeptide can be determined experimentally using a variety of methods. An exemplary method for polypeptide identification and/or determining characteristics for generating a polypeptide identification index is shown in FIG. 1 and described below. The method is useful for defining a polypeptide identification code because the method involves a series of steps, which allow the determination of characteristics associated with a polypeptide, the final step being mass determination of a polypeptide or fragment. The method can include: (i) polypeptide sample preparation; (ii) polypeptide tagging; (iii) optional polypeptide fractionation; (iv) polypeptide fragmentation; (v) polypeptide fragment separation; (vi) affinity isolation of tagged polypeptide fragments; (vii) high resolution polypeptide fragment separation; (viii) database searching; and (ix) polypeptide identification index construction (see Example I).

For polypeptide sample preparation, polypeptide samples for which quantitative proteome analysis is to be performed are isolated from the respective sources using standard protocols for maintaining the solubility of all the polypeptides. Polypeptide samples and preparation of polypeptide samples are discussed in detail below.

For polypeptide tagging, the polypeptides in the sample can be denatured, optionally reduced, and a chemically reactive group of the polypeptides is covalently derivatized with a chemical modification reagent. An exemplary reactive group is a sulfhydryl group that represents a side chain of a reduced cysteine residue, which can be derivatized by a reagent such as ICAT™ (Gygi et al., *Nature Biotechnol.* 17:994-999 (1999)) or IDEnT reagent (Goodlett et al., *Anal. Chem.* 72:1918-1924 (2000)). Other useful reactive groups include amino or carboxyl groups of polypeptides or specific post-translational modifications, including phosphate, carbohydrate or lipid. Any chemical reaction with specificity for a chemical group in the polypeptide can be applied in this step. The ICAT™ type reagent and IDEnT reagents and methods of use are described in more detail below.

For optional polypeptide fractionation, the mixture of tagged polypeptides can be fractionated using any polypeptide separation procedure. A fractionation procedure useful in methods of the invention is reproducible, allows polypeptides to remain soluble, and has a high sample and peak capacity. Any optional fractionation technique can be performed to enrich for low abundance proteins and/or to reduce the complexity of the mixture, while the relative quantities are maintained. Exemplary fractionation methods include, for example, sodium dodecyl sulfate-polyacrylamide gel electrophoresis (SDS-PAGE), chromatographic methods such as size exclusion, ion exchange, and the like, as disclosed herein. Polypeptide fractionation methods are described in more detail below.

For polypeptide fragmentation, the polypeptides in the sample mixture, or the polypeptides contained in each fraction if optional sample fractionation is employed, can be subjected to sequence specific cleavage, such as cleavage by trypsin. The use of sequence specific cleavage can be particularly useful because the termini of peptides cleaved by a sequence specific method can act as a constraint. However, it is understood that the cleavage method used to generate fragments need not be sequence specific, if desired. Methods useful for cleaving polypeptides in a sequence specific manner are described in more detail below.

For polypeptide fragment separation, the resulting polypeptide fragment mixtures can optionally be subjected to a first dimension peptide separation. Separation methods having a high sample capacity, at least moderate resolving power and highly reproducible separation patterns are useful in this step. Examples of first dimension separation methods include anion and cation ion exchange chromatographies. Chromatographic methods are described in more detail below. Although polypeptide fragment separation can optionally be performed, the methods can be advantageously used such that the characteristics of peptide fragments are measured in "bulk," that is, the methods do not require peptide fragment purification to homogeneity.

For affinity isolation of tagged polypeptide fragments, polypeptide fragments can be isolated from each chromatographic fraction using an affinity reagent that binds to the polypeptide tag. For example, polypeptide fragments tagged with the ICAT™ reagent exemplified herein can be isolated using avidin or streptavidin affinity chromatography. An example of a useful affinity medium for isolation of ICAT™ labeled polypeptide fragments is monomeric avidin immobilized on polymer beads. If ICAT™ type reagents with affinity tags different from biotin are used, corresponding affinity media that binds the affinity tag is used.

For high resolution polypeptide fragment separation, liquid chromatography ESI-MS/MS can be used. The polypeptide fragment mixtures eluted from the affinity chromatography columns can be individually analyzed by automated LC-MS/MS using capillary reversed phase chromatography as the separation method (Yates et al., *Methods Mol. Biol.* 112:553-569 (1999)) and data dependent CID with dynamic exclusion (Goodlett, et al., supra, 2000) as the mass spectrometric method.

For database searching, the sequence of polypeptide fragments for which suitable CID spectra were obtained are determined by searching a sequence database from the species under investigation. A sequence database search program such as Sequest (Eng, J. et al., *J. Am. Soc. Mass. Spectrom.* 5:976-989, (1994)) or a program with similar capabilities can be advantageously used to search a database.

For polypeptide identification index construction, the sequences of all the peptides that have been identified by the procedure described above can be entered in a database and annotated with characteristics that were generated during the above-described steps. These attributes can include, for example, partial amino acid composition, the approximate molecular mass of the parent polypeptide, which can be determined, for example, by the optional fractionation step, the order of elution from a first chromatography step, the order of elution time from a second chromatography step, and the like.

Collectively, a sufficient number of characteristics can be determined that distinguish each polypeptide fragment in a polypeptide identification index. The collection of characteristics that uniquely identify a polypeptide represent a "bar code" or polypeptide identification code. Characteristics associated with an unknown polypeptide can be subsequently determined and compared to a previously generated polypeptide identification index. Alternatively, a polypeptide identification index can be determined along with the unknown polypeptide. However, the accumulation of information related to characteristics associated with a polypeptide and collection in an index is convenient for minimizing the experimental steps needed at the time of analyzing a sample. Therefore, a polypeptide identification code that is determined for a fragment of a polypeptide generated in a subsequent experiments can be used to identify a polypeptide in a sample by correlating the polypeptide identification code newly generated for an unknown polypeptide with the polypeptide identification code to identify the unknown polypeptide.

For the identification of a polypeptide by comparison with a polypeptide identification index, a set of characteristics associated with a polypeptide can be determined generally as described above, or can be determined using an equivalent, modified or abbreviated method, or any method that allows for the determination of characteristics associated with a polypeptide. The number of characteristics sufficient to uniquely identify a polypeptide can be readily determined by those skilled in the art. The methods will generally include the identification of 2 or more characteristics, and can include 3 or more, 4 or more, 5 or more, 6 or more, 7 or more, 8 or more, 9 or more, or even 10 or more characteristics, or any number of characteristics so long as a sufficient number of characteristics are determined that distinguish each of the polypeptides in the index.

In generating a polypeptide identification index, characteristics associated with a polypeptide can be used to obtain the polypeptide sequence by searching a sequence database. For example, a partial amino acid sequence of a polypeptide or fragment optionally determined by mass spectrometry can be readily used to search a polypeptide or translated nucleic acid sequence database to identify a name or sequence identification number, such as an accession number, that uniquely describes a polypeptide. A polypeptide identification index can therefore contain polypeptide characteristics such as a common name, a numeric or alphanumeric identification code from a publicly available database, or any other identifying code selected for identifying a polypeptide identification code in a polypeptide identification index.

To obtain sequence information from polypeptides that do not have a parent polypeptide or nucleic acid sequence in a database or that contain an unexpected post-translational modification that presents identification, de novo sequencing can be performed. Identified amino acid sequence can be used to search a polypeptide or nucleic acid sequence database as described above. De novo sequencing can be performed using a variety of methods. A particularly useful method of de novo sequencing involves using a MS dataset generated for polypeptide identification.

It is understood that, although sequence information regarding a polypeptide or portion thereof, for example, determined by a method such as CID, can be included as a characteristic in a polypeptide identification index, the methods of the invention obviate the need to sequence an unknown polypeptide in order to identify it, although sequence information can be included in generating a polypeptide identification index, if desired. Accordingly, a polypeptide identification index can contain information on characteristics associated with a polypeptide that is additional to those characteristics sufficient to identify a polypeptide, for example, sequence information. By accumulating information regarding characteristics associated with a polypeptide in an index, the identity of a polypeptide can be readily determined in the absence of obtaining sequence information on the unknown polypeptide.

A chromatographic separation can be used to determine a characteristic of a polypeptide because the physicochemical properties of a polypeptide are reflected in the behavior of the polypeptide on chromatographic media. For example, a highly charged polypeptide will be eluted from an anion or cation exchange column under specific pH and/or salt conditions that differ from the pH and/or salt conditions under which an uncharged or oppositely charged polypeptide will elute. Therefore, a characteristic associated with a polypeptide can be the particular pH and/or salt condition under which the polypeptide is eluted from a chromatographic column. Similarly, conditions under which a polypeptide elutes from any type of chromatographic column can be determined. An order of elution or buffer condition at which a polypeptide is eluted from a column can be assigned a value to be annotated in a polypeptide index or to be used for comparing with corresponding values in a polypeptide index. A value can be, for example, relative position in an elution profile under defined conditions, a time of elution under a given set of conditions and flow rate, the relative time or order of elution in relation to an external standard fraction number, salt concentration, pH, or any parameter that describes the behavior of a polypeptide on a particular chromatography column that can be reproducibly determined. Alternative methods include gel electrophoresis, for example, isoelectric focusing (IEF) or other analytical electrophoretic methods. Methods for fractionating polypeptides are well known to those skilled in the art (Scopes, *Protein Purification: Principles and Practice*, 3rd ed., Springer Verlag, New York (1993)).

Protein fractionation steps are useful in the methods of the invention for both reducing the complexity of a polypeptide sample prior to mass analysis of a polypeptide or fragment thereof and for determining characteristics associated with a polypeptide. Any of the well known fractionation steps, in addition to chromatographic fractionation described above, can be used to reduce the complexity of the sample and/or serve as a determined characteristic associated with a polypeptide. Exemplary frationation steps include salt precipitation such as ammonium sulfate or precipitation with chemicals such as polyethylene glycol or polyethyleneimine, subcellular fractionation, tissue fractionation, immunoprecipitation, and the like (see Scopes, supra, 1993). A fractionation step can be used to reduce the complexity of a polypeptide population. For example, complexity reduction can be used in the isolation of a polypeptide subpopulation containing polypeptides tagged on a particular amino acid. Furthermore, other fractionation steps such as subcellular fractionation can also be applied to reduce the complexity of a sample and/or provide a characteristic useful for identifying a polypeptide. The fractionation steps can potentially provide biologically important information on the polypeptide, for example, whether the polypeptide is located in an organelle or is a nuclear protein, a membrane protein, and/or part of a signaling complex, and the like. Any fractionation step that advantageously reduces polypeptide population complexity can be applied in the methods of the invention.

A polypeptide fractionation step is useful in the methods of the invention for determining a characteristic associated with a polypeptide. For example, a protein fractionation method based on molecular weight can be used to determine a polypeptide molecular weight. Methods such as SDS-PAGE, commercially available gel elution or preparative cell systems (BIO-RAD), and size exclusion chromatography can be used to determine the apparent molecular weight of a polypeptide or fragment. Polypeptide and/or fragment molecular weight is a characteristic that can be included in a polypeptide identification index.

The particular set of characteristics determined for a polypeptide in generating a polypeptide identification index or for identifying a polypeptide can be selected by the user and will depend on the polypeptide sample, the methods used to prepare the polypeptide sample, the method of mass spectrometry employed and the preferences of the user. The characteristics of a polypeptide can be obtained in any temporal order. For example, polypeptide characteristics can be collected in an order that provides time efficiency or convenience or can be collected as dictated by a particular method selected for sample processing.

In generating a polypeptide index, sequence information, for example, determined by CID, as well as other characteristics of a polypeptide can be used, and the sequence information is particularly useful for correlating other characteristics of a polypeptide with a particular sequence to identify the polypeptide. However, the methods are advantageous in that, once a polypeptide identification index has been generated, obtaining sequence information on a polypeptide is not required. Instead, other characteristics sufficient to identify a polypeptide can be determined, for example, masses and/or ratios between peptides as well as other characteristics, and compared to a polypeptide identification index, which itself can include sequence information, thereby eliminating the need to sequence a polypeptide in order to identify it.

The methods of the invention for generating a polypeptide identification index involve determining a set of characteristics associated with a first and second polypeptide in which the determined characteristics are sufficient to distinguish the first and second polypeptides. Characteristics that are sufficient to distinguish the first and second polypeptides refer to a set of characteristics that can be uniquely attributed to a polypeptide so that the polypeptide identity can be determined unambiguously. In a case in which set of characteristics is shared by one or more polypeptides, an additional characteristic that allows a polypeptide to be distinguished from another polypeptide is determined. Thus, the polypeptides represented in a polypeptide identification index can be distinguished from each other by the set of characteristics that identify each polypeptide.

The methods of the invention for identifying a polypeptide can be applied to a population of polypeptides in which two or more polypeptides are identified and can be conveniently used to identify multiple polypeptides in a sample simultaneously, if desired. Therefore, the method can be applied to a simple or complex polypeptide sample. A simple polypeptide sample can be, for example, a purified polypeptide sample containing one to several polypeptides. A complex sample can be, for example, a cell lysate or fraction containing a few to several hundred polypeptides or even thousands or tens of thousands of polypeptides. Using the methods described herein, the determination of polypeptide characteristics can require the collection of experimental data resulting from a series of steps, such as, for example, a series of chromatographic separations.

An exemplary process useful for organizing data obtained during analysis of complex polypeptide samples involves parceling information into theoretical "bins". For example, an ICAT™ type-labeled mixture of polypeptides can be separated by size into a particular number of bins, which can be fractions eluting from chromatography column, such as size exclusion, ion exchange, and the like, or segments of an SDS polyacrylamide gel. The polypeptides in each bin can be fragmented by a sequence specific cleavage method. Alternatively, analysis of polypeptides in a sample can be performed without fractionating the polypeptides so long as there has been a sufficient reduction in complexity of the sample to allow the identification of the polypeptide without fractionation. The peptide mixture, which has been fractionated into bins, can be further fractionated by various methods, including, for example, ion exchange chromatography, affinity chromatography such as is used with the isolation of ICAT™ type labeled peptides, or reverse phase liquid chromatography. Each bin of peptides can then be further binned by ion exchange chromatography and once again divided further into a particular number of bins. Each of these bins can be further separated by reverse phase chromatography and divided further into a particular number of bins, each of which can be analyzed by mass spectrometry. Hence each polypeptide analyzed by such a method will have five associated characteristics that can be represented, for example, as a 5-digit polypeptide identification code or "bar code" based on cysteine content, size, charge, hydrophobicity, and mass.

The methods of the invention for indexing characteristics associated with a large number of polypeptides use an amount of computer memory that is quadratic in sequence length. An advanced data structure such as, for example, suffix trees, can be used to reduce the requirements of computer memory (Gusfield, *Algorithms on Strings, Trees and Sequences: Computer Science and Computational Biology*, Cambridge University Press (1997)). Suffix trees are a compact data representation for all suffixes in a database of sequences. In their pure form, they can be constructed in linear time and stored in linear, instead of quadratic memory. Various modifications of suffix trees and traversal algorithms can be used to optimize computation time and use of computer memory associated with searching a polypeptide identification index.

A set of determined characteristics associated with a polypeptide are compared to a polypeptide identification index. Various search algorithms can be employed for matching values assigned to determined characteristics with annotated values in the index. A useful strategy for increasing the efficiency of database searching is the narrowing or "constraining" of the database. The term "constrain" when used in reference to a polypeptide identification index refers to a limitation that is applied to a polypeptide identification index in order to obtain a subindex containing a fraction of polypeptide identification codes corresponding to polypeptides having characteristics that match one or characteristics of a polypeptide to be identified. A subindex can be generated when a group of polypeptides having a common characteristic is selected out of a polypeptide identification index or when a particular characteristic contained in a polypeptide identification code is used to omit one or more polypeptides from an index. A common characteristic can be a definite physicochemical characteristic such as a partial amino acid sequence or any other determined characteristic assigned a range of values. For example, a mass of a polypeptide fragment expressed as a range of values that account for the error in mass determination can serve as a constraint for selecting a subset of polypeptides or fragments of a particular mass.

One characteristic associated with a polypeptide that can be used to contrain a database is partial amino acid composition. The partial amino acid composition of a polypeptide includes the identification of a single amino acid present in a particular polypeptide or fragment thereof. A partial amino acid sequence can be obtained, for example, by treating a polypeptide or fragment thereof with a reagent that results in the generation of a polypeptide or fragment that contains one or more defined amino acids. For example, a sequence specific polypeptide cleavage method will produce fragments with one or more known amino acid residues at the fragment carboxy- or amino-terminus. However, it is not necessary to know if a specific amino acid residue is located at the fragment carboxy- or amino-terminus of a polypeptide. Accordingly, cleavage of a polypeptide with a sequence specific protease indicates the presence of the corresponding amino acid and/or sequence in the polypeptide or peptide fragment thereof. Similarly, a reagent can be used to specifically modify or label one or more specific amino acid residues of a polypeptide or fragment. A polypeptide or fragment that contains such a modification or label will be known to contain a specific amino acid. Partial amino acid composition is a characteristic associated with a polypeptide that can be useful for constraining a polypeptide identification index to generate a polypeptide identification subindex.

The comparison of a set of determined characteristics with a polypeptide identification index can therefore involve a series of searches constrained by a determined characteristic of a polypeptide. For example, an initial search of parent polypeptide or fragment mass can be performed, resulting in the generation of a polypeptide identification subindex containing polypeptide and fragment mass values that are similar to, that is, within the range of instrument error, the polypeptide or fragment thereof to be identified. A second characteristic to be searched against the generated polypeptide identification subindex, such as the presence of a cysteine residue in the polypeptide to be identified, provides a further constraint and can be used to generate a further polypeptide identification subindex.

The determined mass of a polypeptide or fragment is a characteristic that can be advantageously used to constrain such a database search to increase the efficiency of searching a large database. For example, tandem MS spectra can be analyzed using software such as SEQUEST, which generates a list of peptides in a database that match the molecular mass of the unknown peptide on which CID was carried out and then compared the observed CID spectrum of the unknown with that for all possible isobars (Eng, J. et al., *J. Am. Soc. Mass. Spectrom.* 5:976-989, (1994)). Therefore, the set of peptides having a molecular mass similar to the polypeptide fragment being analyzed generated by this type of search provides a subset of possible parent polypeptides represented by the polypeptide fragment. The subset can then be searched using, for example, a partial amino acid composition, to identify the parent polypeptide. Those skilled in the art will know or can readily determine appropriate correlation score parameters for a particular search using software applications such as SEQUEST.

The method of comparing two or more polypeptide populations employs a method for quantitatively distinguishing the two polypeptide populations, such as the method described herein using an ICAT™ type reagent and is illustrated in FIG. 3. Two or several chemically identical but differentially isotopically labeled ICAT™ type reagents can be used at this step. Therefore, although FIG. 3 depicts two samples, multiple samples can be compared using the methods described herein. The samples depicted in FIG. 3 contain polypeptide populations harvested from the same sample type that differ from each other in growth condition. Exemplary differential growth conditions can include growth under different metabolic conditions or cells at different metabolic states, comparison of a normal and disease sample such as a tumor sample, comparison of untreated versus cells treated with a pharmacological agent, and the like.

As shown in FIG. 3, the samples are independently labeled using an ICAT™ type reagent, combined, and characteristics of the polypeptides and corresponding fragments are determined, as described herein. Polypeptides and fragments generated during this process can be analyzed using single stage mass spectrometry, rather than by MS/MS, if desired, to increase sample throughput and sensitivity (Goodlett et al., supra, 2000). The characteristics determined for polypeptides and fragments are used to determine polypeptide identities, as described herein. Subsequently, the mass spectra can be examined for pairs of peptide ions that co-fractionated throughout the process and that have a mass difference that precisely corresponds to the mass difference encoded in the ICAT™ type reagent. The relative signal intensities of the two peaks indicate the relative abundance of the fragment polypeptides and therefore indicate the relative abundance of the corresponding parent polypeptide initially present in the sample. Therefore, a method for comparing the polypeptides contained in two polypeptide samples can involve the generation of two reference polypeptide indices that contain, for each polypeptide identified, a quantitative determination of polypeptide amount in addition to a polypeptide identification code.

An alternative method for comparing two or more polypeptide populations is the comparison of one or more polypeptide samples to a previously determined polypeptide reference index. A set of characteristics of one of more polypeptides in a polypeptide sample can be identified and compared to a reference polypeptide identification index to determine the identities of one or more polypeptides and comparative quantities of the identified polypeptides. If desired, an unknown sample can be compared to a reference sample using the above-described quantitative methods to determine relative expression levels of the polypeptides. A reference sample can be, for example, a sample from a healthy individual or a sample from a control condition useful for comparing to the physiological state of another sample such as a disease sample.

A polypeptide identification index that contains quantitative determinations of polypeptide amount is considered to be a "polypeptide profile" of the particular sample used to generate the index. A polypeptide profile, as used herein, is a set of polypeptide identification codes that includes polypeptide amount, generated for a specific sample.

A polypeptide profile is useful in methods of proteomics because such a profile can be used to distinguish between different conditions or states of cells, tissues, organs, and organisms. The polypeptides expressed by a cell or tissue at a particular time can be used to define the state of the cell or tissue at the time of measurement. Therefore, quantitative and qualitative differences between the polypeptide profiles of the same cell type in different states can be used to diagnose the respective states. Examples for such comparisons include normal versus tumor cells, cells at different metabolic states and untreated cell versus cells treated with specific pharmacological agents. The differences between two polypeptide profiles can be described as a "differential polypeptide profile".

A differential polypeptide profile is useful for analyzing quantitative changes in the polypeptides contained in samples derived from different cell types such as, for example, cancerous and normal cells, stimulated and unstimulated cells, or from different tissue samples of clinical interest.

The methods of the invention for generating differential polypeptide profiles are applicable to the analysis of changes in the polypeptide profiles in samples such as body fluids. A differential polypeptide profile is determined by comparing the polypeptide profile of two specimens, for example, a normal to disease-related polypeptide profile. For example, a polypeptide profile representative of a normal specimen state can be generated and compared to a specimen suspected to be in an abnormal or disease state. Alternatively, a reference polypeptide profile representative of a disease state can be compared with a specimen from an individual having or suspected of having a particular disease state. A reference polypeptide profile representative of a normal or disease state can be determined using a specimen from a particular individual or a population of individuals.

If desired, analysis can be performed on a population rather than an individual, particularly a reference population or control population. Such a reference population can be used for comparison of an unknown sample. One skilled in the art can determine an appropriate reference population based on the particular application of the methods of the invention. The methods of the invention can be used to generate a differential polypeptide profile that identifies the differences in polypeptide expression between two samples, for example, a normal and disease state. The size of the reference population depends on the criteria used to select reference individuals. Depending on the selection criteria and particular application of the methods of the invention, a reference population can be a relatively small number to a large number of individuals, including thousands of individuals.

The large-scale analysis of samples from patients having specifically diagnosed diseases or exhibiting signs or symptoms of a disease is useful for identifying clinical markers or constellations of markers for the respective conditions. Samples from an individual having a disease can be used to generate a qualitative and/or quantitative polypeptide identification index for that disease. Similarly, the comparative analysis of polypeptides contained in samples from patients undergoing therapeutic treatment can be used to identify diagnostic markers or constellation of markers indicating the success or failure of the treatment. The methods are also applicable to the analysis of such samples on a systematic, population-wide scale for the discovery or screening of markers or constellations of markers useful for indicating the predisposition of individuals for certain clinical conditions.

The invention further provides a method for generating a polypeptide identification index. The method includes steps of (a) determining a set of two or more characteristics associated with a first polypeptide, or a peptide fragment thereof, one of the characteristics being the mass of a peptide fragment of the polypeptide, the peptide fragment mass being determined by mass spectrometry; (b) repeating step (a) for a second polypeptide; (c) optionally determining one or more additional characteristics associated with the first and second polypeptides, wherein the determined characteristics are sufficient to distinguish the first and second polypeptides, thereby generating a polypeptide identification index for the first and second polypeptides. The method can further comprise repeating steps (a) through (c) one or more times for a different polypeptide, wherein the determined characteristics are sufficient to distinguish each of the polypeptides, thereby generating a polypeptide identification index for each of the polypeptides. As with determining characteristics of a polypeptide, the polypeptide identification index can be determined with any of the methods disclosed herein for determining characteristics associated with a polypeptide. The polypeptide identification index can optionally be obtained by determining mass in the absence of ion selection.

The methods of the invention for generating a polypeptide identification index involve the determination of polypeptide or fragment mass in the absence of ion selection for producing fragment ions and can further involve the determination of a fragment mass at an accuracy of greater than 1 part per million, or even lower accuracy (higher ppm), if desired. Although a polypeptide identification index can contain a polypeptide amino acid sequence, it is not required that a polypeptide or fragment be sequenced for practicing the methods of the invention for generating a polypeptide identification index.

The invention further provides a method for identifying a polypeptide. The method includes steps of (a) simultaneously determining the mass of a subset of parent polypeptides from a population of polypeptides and the mass of peptide fragments of the subset of parent polypeptides; (b) comparing the determined masses to a polypeptide identification index; and (c) identifying one or more polypeptides of the polypeptide identification index having the determined masses. The method can further comprise the steps of (d) determining one or more additional characteristics associated with one or more of the parent polypeptides; (e) comparing the characteristics determined in step (a) and step (d) to the polypeptide identification index; and (f) optionally repeating steps (d) and (e) one or more times, wherein a set of characteristics is determined that identifies a parent polypeptide as a single polypeptide in the polypeptide identification index.

The method of the invention for identifying a polypeptide includes a step of simultaneously determining the mass of a subset of parent polypeptides from a population of polypeptides and the mass of polypeptide fragments of the subset of parent polypeptides (see Example II). The simultaneous determination of masses of a subset of parent polypeptides refers to the acquisition of a subset of parent polypeptide mass values from a single sample containing a polypeptide population. The term "simultaneous" is intended to mean that the masses of parent polypeptides and polypeptide fragments are determined concurrently such that the MS method used can acquire masses of parent polypeptides and corresponding fragments in a time frame sufficient that parent and fragment masses can be correlated to the same subset of polypeptides. For example, the polypeptides being sampled in a MS method will change over time as different subsets of polypeptides elute from a chromatographic column as dictated by the flow rate of the column. A simultaneous determination occurs during a time period before a particular subset of polypeptides is altered due to the introduction of an additional polypeptide or loss of a polypeptide of the polypeptide subset that occurs as a result of on-line sampling methods.

Simultaneous determination of the mass of a subset of polypeptides can be performed, for example, in the absence of selection of a single ion for mass determination. For example, several polypeptides can be selected rather than a single ion (Masselon et al., *Anal. Chem.* 72:1918-1924 (2000)). In methods of the invention, preferably greater than 5 ions, for example, 6 ions, 7 ions, 8 ions, 9 ions, 10 ions, or even greater numbers of ions are selected. In such a case, the polypeptide identification index is preferably an annotated polypeptide index.

Alternatively, simultaneous determination of masses of a subset of polypeptides can be performed in the absence of single ion selection or in the absence of ion selection in a source region (see FIG. 2). In such a case, the fragment ions obtained are deconvoluted to determine which ions are associated with a particular parent polypeptide and therefore useful as a characteristic associated with the parent polypeptide. Such a method can be useful for detecting and identifying less abundant ions that are not selected for fragmentation in standard MS methods.

A mass spectrometry method useful for obtaining polypeptide and polypeptide fragment masses simultaneously is in-source CID on ESI-TOF. The method involves continuously alternating between parent ion and in-source CID scans. In-source CID scans provide specific fragment ions traceable to a given parent ion even in the presence of multiply fragmented parent ions. Parent-fragment ion lineages can be determined by deconvolution of mass spectrometry data using appropriate software. MS instruments providing lower accuracy measurements, for example, ESI-TOF, can be used advantageously for providing unique constraints for polypeptide identification.

The methods of the invention involve determining characteristics associated with a polypeptide. A sample containing a polypeptide can be as simple as an isolated polypeptide mixture containing a polypeptide or as complex as sample containing all of the polypeptides expressed in an organism. Furthermore, a sample can be fractionated, if desired, using the methods disclosed herein.

A polypeptide can be in a sample isolated from a variety of sources. For example, a polypeptide sample can be prepared from any biological fluid, cell, tissue, organ or portion thereof, or any species of organism. A sample can be present in an individual and obtained or derived from the individual. For example, a sample can be a histologic section of a specimen obtained by biopsy, or cells that are placed in or adapted to tissue culture. A sample further can be a subcellular fraction or extract. A sample can be prepared by methods known in the art suitable for maintaining polypeptide solubility, such as those described herein.

A specimen refers specifically to a sample obtained from an individual. A specimen can be obtained from an individual as a fluid or tissue specimen. For example, a tissue specimen can be obtained as a biopsy such as a skin biopsy, tissue biopsy or tumor biopsy. A fluid specimen can be blood, serum, urine, saliva, cerebrospinal fluid or other bodily fluids. A fluid specimen is particularly useful in methods of the invention since fluid specimens are readily obtained from an individual. Methods for collection of specimens are well known to those skilled in the art (see, for example, Young and Bermes, in *Tietz Textbook of Clinical Chemistry*, 3rd ed., Burtis and Ashwood, eds., W. B. Saunders, Philadelphia, Chapter 2, pp. 42-72 (1999)).

A polypeptide to be used in the methods of the invention can be obtained from a source such as a cell, tissue, organ or organism. A variety of methods are known in the art for lysing a cell. Cells can be lysed, for example, by denaturants, one or more cycles of freezing and thawing, and sonication. Following lysis, the polypeptide mixture can be subjected to a fractionation to remove, for example, nucleic acid or lipid, or to remove intact subcellular fractions or organelles. Methods of lysing and fractionating cells are well known to those skilled in the art (see Scopes, supra, 1993).

For identification of a polypeptide, a sample or specimen can be contained in a buffer suitable for maintaining polypeptide solubility such as, for example, a buffer containing a detergent, including denaturants such as sodium dodecyl sulfate (SDS). Denaturants useful for solubilizing polypeptides include, for example, guanidine-HCl, guanidine-isothiocyanate and urea. In the case of guanidine-isothiocyanate, as with treatment with any reagent that can covalently modify a polypeptide, such reagents can be used so long as the polypeptide identification index to which the sample is to be compared has been prepared in substantially the same manner as the sample sufficient for comparison of the same polypeptide. Other denaturants well known in the art can be similarly used for solubilizing polypeptides. In addition, reducing agents such as dithiothreitol (DTT), dithioerythritol (DTE), or mercaptoethanol can be included.

The methods of the invention can optionally involve protein fractionation steps. Protein fractionation refers to any method useful for removing one or more polypeptides from a polypeptide population. Fractionation can include, for example, a centrifugation step that separates soluble from insoluble components, a method of electrophoresis, and a method of chromatography, or any of the methods disclosed. For chromatographic separation, a wide variety of chromatographic media well known in the art can be used to separate polypeptide populations. For example, polypeptides can be separated based on size, charge, hydrophobicity, binding to particular dyes and other moieties associated with chromatographic media. Size exclusion, gel filtration and gel permeation resins are useful for polypeptide separation based on size. Examples of chromatographic media for charge-based separation are strong and weak anion exchange and strong and weak cation exchange resins. Hydrophobic or reverse phase chromatography can also be used.

Affinity chromatography can also be used including, for example, dye-binding resins such as Cibacron blue, substrate analogs, including analogs of cofactors such as ATP, NAD, and the like, ligands, specific antibodies, either polyclonal or monoclonal, and the like. An exemplary affinnity resin includes affinity resins that bind to specific moieties that can be incorporated into a polypeptide such as an avidin resin that binds to a biotin tag on a polypeptide, as disclosed herein. The resolution and capacity of particular chromatographic media are known in the art and can be determined by those skilled in the art. The usefulness of a particular chromatographic separation for a particular application can similarly be assessed by those skilled in the art.

Those of skill in the art will be able to determine the appropriate chromatography conditions for a particular sample size or composition and will know how to obtain reproducible results for chromatographic separations under defined buffer, column dimension, and flow rate conditions. All protein fractionation methods can optionally include the use of an internal standard for assessing the reproducibility of a particular chromatographic application. Appropriate internal standards will vary depending on the chromatographic medium. Those skilled in the art will be able to determine an internal standard applicable to a method of chromatography.

Polypeptide tagging is useful in the methods of the invention for reducing polypeptide sample complexity, providing a database search constraint, and enabling quantitative polypeptide comparisons. The complexity of a polypeptide sample can be reduced by tagging a polypeptide with an affinity tag that can be used for isolating a subpopulation of polypeptides that contain the tag. For example, a population of polypeptides and fragments can be labeled on a relatively rare amino acid, such as cysteine, and a subpopulation of polypeptides and fragments containing the tag can be isolated. The subpopulation of polypeptides and fragments isolated in this manner will thus contain a known amino acid. As described herein, a known amino acid constitutes a partial amino acid composition which is useful for constraining a database search. Quantitative polypeptide comparisons can be performed by differentially tagging two polypeptides or polypeptide populations. An ICAT™ type affinity reagent, described in more detail below, is particularly useful for this purpose, although any other method of polypeptide tagging can be similarly applied to polypeptide comparisons.

Polypeptide tagging can be performed using a variety of methods known in the art. A reagent for polypeptide tagging or modification can contain various components that are separated by linker regions. Components of a polypeptide tagging reagent can include a reactive group that modifies a specific chemical group of a polypeptide, a moiety that can be detected, such as by mass spectrometry, and an affinity tag to be used for polypeptide isolation. Two examples of polypeptide tagging reagents, ICAT™ type and IDEnT, are described in detail below, although any type of polypeptide tag can be used, if desired.

The methods of the invention for quantitatively comparing two polypeptide populations involve the use of the isotope-coded affinity tag (ICAT™) method (Gygi et al., *Nature Biotechnol.* 17:994-999 (1999) which is incorporated herein by reference). An ICAT™ type reagent can additionally be useful for polypeptide tagging applications that do not involve quantitative comparisons. The ICAT™ type reagent method uses an affinity tag that can be differentially labeled with an isotope that is readily distinguished using mass spectrometry, for example, hydrogen and deuterium. The ICAT™ type affinity reagent consists of three elements, an affinity tag, a linker and a reactive group.

One element of the ICAT™ type affinity reagent is an affinity tag that allows isolation of peptides coupled to the affinity reagent by binding to a cognate binding partner of the affinity tag. A particularly useful affinity tag is biotin, which binds with high affinity to its cognate binding partner avidin, or related molecules such as streptavidin, and is therefore stable to further biochemical manipulations. Any affinity tag can be used so long as it provides sufficient binding affinity to its cognate binding partner to allow isolation of peptides coupled to the ICAT™ type affinity reagent. An affinity tag can also be used to isolate a tagged peptide with magnetic beads or other magnetic format suitable to isolate a magnetic affinity tag. In the ICAT™ type reagent method, or any other method of affinity tagging a peptide, the use of covalent trapping can be used to bind the tagged peptides to a solid support, if desired.

A second element of the ICAT™ type affinity reagent is a linker that can incorporate a stable isotope. The linker has a sufficient length to allow the reactive group to bind to a specimen polypeptide and the affinity tag to bind to its cognate binding partner. The linker also has an appropriate composition to allow incorporation of a stable isotope at one or more atoms. A particularly useful stable isotope pair is hydrogen and deuterium, which can be readily distinguished using mass spectrometry as light and heavy forms, respectively. Any of a number of isotopic atoms can be incorporated into the linker so long as the heavy and light forms can be distinguished using mass spectrometry. Exemplary linkers include the 4,7,10-trioxa-1,13-tridecanediamine based linker and its related deuterated form, 2,2',3,3',11,11',12,12'-octadeutero-4,7,10-trioxa-1,13-tridecanediamine, described by Gygi et al. (supra, 1999). One skilled in the art can readily determine any of a number of appropriate linkers useful in an ICAT™ type affinity reagent that satisfy the above-described criteria.

The third element of the ICAT™ type affinity reagent is a reactive group, which can be covalently coupled to a polypeptide in a specimen. Methods for modifying side chain amino acids in polypeptides are well known to those skilled in the art (see, for example, Glazer et al., *Laboratory Techniques in Biochemistry and Molecular Biology: Chemical Modification of Proteins*, Chapter 3, pp. 68-120, Elsevier Biomedical Press, New York (1975); Pierce Catalog (1994), Pierce, Rockford Ill.). Any of a variety of reactive groups can be incorporated into an ICAT™ type affinity reagent so long as the reactive group can be covalently coupled to a polypeptide. For example, a polypeptide can be coupled to the ICAT™ type affinity reagent via a sulfhydryl reactive group, which can react with free sulfhydryls of cysteine or reduced cystines in a polypeptide. An exemplary sulfhydryl reactive group includes an iodoacetamido group, as described in Gygi et al. (supra, 1999). Other examplary sulfhydryl reactive groups include maleimides, alkyl and aryl halides, α-haloacyls and pyridyl disulfides. If desired, the polypeptides can be reduced prior to reacting with an ICAT™ type affinity reagent, which is particularly useful when the ICAT™ type affinity reagent contains a sulfhydryl reactive group.

A reactive group can also react with amines such as Lys, for example, imidoesters and N-hydroxysuccinimidyl esters. A reactive group can also react with carboxyl groups found in Asp or Glu, or the reactive group can react with other amino acids such as His, Tyr, Arg, and Met. A reactive group can also react with a phosphate group for selective labeling of phosphopeptides, or with other covalently modified peptides, including glycopeptides, lipopeptides, or any of the covalent polypeptide modifications disclosed herein. One skilled in the art can readily determine conditions for modifying specimen molecules by using various reagents, incubation conditions and time of incubation to obtain conditions optimal for modification of specimen molecule for use in methods of the invention.

The ICAT™ type reagent method is based on derivatizing a specimen molecule such as a polypeptide with an ICAT™ type affinity reagent. A control reference specimen and a specimen from an individual to be tested are differentially labeled with the light and heavy forms of the ICAT™ type affinity reagent. The derivatized specimens are combined, and the derivatized molecules cleaved to generate fragments. For example, a polypeptide molecule can be enzymatically cleaved with one or more proteases into peptide fragments. Exemplary proteases useful for cleaving polypeptides include trypsin, chymotrypsin, pepsin, papain, *Staphylococcus aureus* (V8) protease, and the like. Polypeptides can also be cleaved chemically, for example, using CNBr, acid or other chemical reagents.

Once cleaved into fragments, the tagged fragments derivatized with the ICAT™ type affinity reagent are isolated via the affinity tag, for example, biotinylated fragments can be isolated by binding to avidin in a solid phase or chromatographic format. If desired, the isolated, tagged fragments can be further fractionated using one or more alternative separation techniques, including ion exchange, reverse phase, size exclusion affinity chromatography and the like, or electrophoretic methods, including isoelectric focusing. For example, the isolated, tagged fragments can be fractionated by high performance liquid chromatography (HPLC), including microcapillary HPLC.

The fragments are analyzed using mass spectrometry (MS). Because the specimen molecules are differentially labeled with light and heavy affinity tags, the peptide fragments can be distinguished on MS, allowing a side-by-side comparison of the relative amounts of each peptide fragment from the control reference and test specimens. If desired, MS can also be used to sequence the corresponding labeled peptides, allowing identification of molecules corresponding to the tagged peptide fragments.

An advantage of the ICAT™ type reagent method is that the pair of peptides tagged with light and heavy ICAT™ type reagents are chemically identical and therefore serve as mutual internal standards for accurate quantification (Gygi et al., supra, 1999). Using MS, the ratios between the intensities of the lower and upper mass components of pairs of heavy- and light-tagged fragments provides an accurate measure of the relative abundance of the peptide fragments. Thus, the ICAT™ type reagent method can be conveniently used to identify differentially expressed polypeptides, if desired.

An IDEnT reagent can be used to modify a polypeptide by introducing an isotopic tag at a specific protein functional group. An exemplary IDEnT reagent is described in Goodlett et al., supra, 2000. An IDEnT reagent contains at least one element with an isotopic distribution that creates a unique signature in a mass spectrometer. For example, an IDEnT reagent can contain chlorine, deuterium, or another element, including a radioactive element. An IDEnT reagent can be designed to bind to a low abundance amino acid in a polypeptide, such as cysteine. The labeling of a polypeptide with an IDEnT tag can be applied to the methods of the invention by providing a constraint for searching a polypeptide identification index with polypeptide fragment masses.

Protein cleavage or fragmentation is useful in the methods of the invention for providing a contraint for database searching. Polypeptide fragmentation can be sequence-specific or non-specific. Sequence-specific polypeptide cleavage provides the advantage of obtaining polypeptide fragments that contain known amino acids which can be used to constrain a database search. Examples of reagents useful for performing non-specific polypeptide cleavage are papain, pepsin and protease Sg. These proteases can be used to achieve a desired degree of protein fragmentation, such as, for example, the generation of about two to four polypeptide fragments from a polypeptide by altering the reaction conditions. Conditions for using these proteases are well known in the art. Examples of reagents useful for performing sequence-specific polypeptide cleavage are trypsin, V-8 protease, o-iodosobenzoic acid, cyanogen bromide and acid.

The invention also provides a polypeptide identification index for identifying a polypeptide from a population of polypeptides. The index comprises an annotated set of characteristics associated with polypeptides in the index, one of the characteristics being the mass of a fragment of the polypeptide, the fragment mass being determined by mass spectrometry in the absence of ion selection for producing fragment ions. The characteristics are sufficient to distinguish one of the polypeptides from other polypeptides in the index. A polypeptide identification index can comprise characteristics for 2 or more, 3 or more, 5 or more, 10 or more, 20 or more, 50 or more, 100 or more, 200 or more, 500 or more, 1000 or more, 2000 or more, 5000 or more, or even 10,000 or more polypeptides. A polypeptide identification index can also include substantially all of the polypeptides in a sample. For example, a polypeptide identification index can include substantially all of the polypeptides expressed in a genome, such as a viral, bacterial, plant, or animal genome, including a mammalian genome such as human, non-human primates, mouse, rat, bovine, goat, rabbit, or other mammalian species. The number of polypeptides in a polypeptide identification index will depend on the needs of the user and will vary depending on the source of the sample to be used to identify polypeptides and the complexity of polypeptide expression in the sample.

The polypeptide identification index can be directed to a whole organism or to particular tissues or cells in an organism or to specific subcellular fractions, for example, organelles, as desired. Accordingly, similar to the reduction in complexity applied to a sample to be tested, a polypeptide identification index directed to a particular target such as an organism, tissue, cell or subcellular fraction, can be useful for simplifying a search for identification of a particular polypeptide in a particular application. For example, in a particular diagnostic application where expression of a particular polypeptide or group of polypeptides, or the amount of expression of the polypeptides, is correlated with a particular condition such as a disease condition, the use of a polypeptide identification index directed to a relevant target can be used. For example, if a group of nuclear proteins are known to be overexpressed in a cancer cell, the use of a polypeptide identification index directed to nuclear proteins can be used to test for overexpression of the nuclear proteins in a sample from an individual using the quantitative methods disclosed herein. Moreover, the generation of a targeted polypeptide identification index and comparison to a relevant disease sample can be used to identify aberrantly expressed polypeptides, which in turn can be used in diagnostic applications, as disclosed herein.

The invention additionally provides a polypeptide identification index comprising an annotated set of characteristics associated with polypeptides of the index comprising two or more characteristics associated with polypeptides of the index, or a fragment thereof, one of the characteristics being the mass of a fragment of the polypeptide, the fragment mass being determined by mass spectrometry in the absence of ion selection for producing fragment ions, and wherein the mass is determined at an accuracy in ppm of greater than 1 ppm.

If desired, a polypeptide identification index can be conveniently stored on a computer readable medium. Accordingly, the invention provides a computer readable medium comprising an invention polypeptide identification index, for example, an annotated polypeptide index. Such a computer readable medium comprising a polypeptide identification index is useful for comparing the characteristics of a polypeptide with the polypeptide identification index, which can be conveniently performed on a computer apparatus. The use of a computer apparatus is convenient since a polypeptide identification index can be conveniently stored and accessed for comparison to characteristics and/or quantitative amounts of a polypeptide in a sample. A polypeptide identification index can be conveniently accessed using appropriate hardware, software, and/or networking, for example, using hardware interfaced with networks, including the internet.

By using various hardware, software and network combinations, the methods of the invention including the step of comparing the characteristics determined for a polypeptide to a polypeptide identification index can be conveniently performed in a variety of configurations. Accordingly, the invention additionally provides a computer apparatus for carrying out computer executable steps corresponding to steps of invention methods. For example, a single computer apparatus can contain instructions for carrying out the computer executable step(s) of comparing characteristics determined for polypeptide to a polypeptide identification index, a polypeptide identification index, and instructions for determining whether the characteristics determined for the polypeptide correspond to one or more polypeptides in the polypeptide identification index.

Alternatively, the computer apparatus can contain instructions for carrying out the steps of an invention method while the polypeptide identification index is stored on a separate medium. In addition, instructions for determining whether a polypeptide corresponds to one or more polypeptides in the polypeptide identification index can be contained on a separate computer apparatus or separate medium, or combined with the computer apparatus containing the computer executable steps of the method and/or the database on a separate medium. Such a separate computer readable medium can be another computer apparatus, a storage medium such as a floppy disk, Zip disk or a server such as a file-server, which can be accessed by a carrier wave such as an electromagnetic carrier wave. Thus, a computer apparatus containing a polypeptide identification index or a file-server on which the polypeptide identification index is stored can be remotely accessed via a network such as the internet. One skilled in the art will know or can readily determine appropriate hardware, software or network interfaces that allow interconnection of an invention computer apparatus.

It is understood that modifications which do not substantially affect the activity of the various embodiments of this invention are also included within the definition of the invention provided herein. Accordingly, the following examples are intended to illustrate but not limit the present invention.

EXAMPLE I

Generation of an Annotated Polypeptide Index

This example describes the generation of an annotated polypeptide index and use of the annotated polypeptide index to identify a polypeptide in a sample.

The elements of an annotated polypeptide (AP) index, also referred to as an annotated peptide tag (APT) index or database, are the sequences of essentially all the peptides or selected peptides with specific structural features that are generated by sequence specific chemical or enzymatic fragmentation of the proteins produced by the species, cell or tissue under investigation. Each peptide is annotated with attributes, or characteristics, that are easily determined experimentally and that permit the unambiguous correlation between the annotated peptide and the protein from which the peptide originated.

The generation of an exemplary AP index can involve the following specific steps: harvest proteins; label proteins with an isotope coded affinity tag (ICAT™) type reagent; fractionate proteins by molecular weight; digest proteins with a protease, for example, trypsin, to generate peptides; separate peptides by chromatography, for example, ion exchange chromatography; purify each ion exchange fraction by affinity chromatography, for example, based on the ICAT™ type affinity tag; analyze each affinity chromatography fraction by LC/MS/MS or CE/MS/MS; identify essentially all expressed proteins via a database search of individual MS/MS peptide spectra; and generate a database of annotated peptide tags that constitute a unique bar code for an individual peptide based on measured physicochemical properties and thus the parent protein of that peptide.

The AP index can be generated as follows: (i) protein sample preparation; (ii) protein tagging; (iii) optional protein fractionation; (iv) protein fragmentation; (v) peptide separation; (vi) affinity isolation of tagged peptides; (vii) high resolution peptide separation; (viii) database searching; (ix) AP index (APT database) construction.

(i) Protein Sample Preparation. Protein samples for which quantitative proteome analysis is to be performed, for example, cells, tissues, subcellular fractions, body fluids, cellular secretions, and the like, are isolated from the respective sources using standard protocols for maintaining the solubility of all the proteins.

(ii) Protein tagging. The proteins in the sample are completely denatured, reduced, and the all the sulfhydryl groups representing the side chains of reduced cysteine residues are covalently derivatized with the light or heavy form, respectively, of sulfhydryl-specific ICAT™ type reagents using the conditions described previously (Gygi et al., Nature Biotechnol. 17:994-999 (1999))(see FIG. 3. While cysteine tagging is a particularly useful implementation of the method, any other chemical reaction with specificity for a chemical group in the protein can also be applied.

(iii) Optional Protein Fractionation. The mixture of tagged proteins is fractionated using any one of the known standard protein separation procedures. The applied procedure is reproducible, maintains the proteins in solution, and has a high sample capacity. A particularly useful method is preparative sodium dodecyl sulfate-polyacrylamide gel electrophoresis (SDS-PAGE).

(iv) Protein Fragmentation. The proteins in the sample mixture, or the proteins contained in each fraction if optional sample fractionation is employed, are subjected to sequence specific cleavage. A preferred method is tryptic cleavage.

(v) Peptide Separation. The resulting peptide mixtures are subjected to a first dimension peptide separation. The peptide separation method has a high sample capacity, at least moderate resolving power, and generates highly reproducible separation patters, irrespective of the complexity of the sample applied. A particularly useful first dimension separation method is cation ion exchange chromatography.

(vi) Affinity Isolation of Tagged Peptides. Peptides tagged with the ICAT™ type reagent, i.e., cysteine containing peptides, are isolated from each chromatographic fraction using avidin or streptavidin affinity chromatography. A particularly useful affinity medium is monomeric avidin immobilized on polymer beads. If ICAT™ type reagents with affinity tags different from biotin are used, affinity media complementary to that tag are used.

(vii) High Resolution Peptide Separation. A particularly useful method for high resolution peptide separation is liquid chromatography ESI-MS/MS. The peptide mixtures eluted from the affinity chromatography columns are individually analyzed by automated LC-MS/MS using capillary reversed phase chromatography as the separation method (Yates et al., Methods Mol. Biol. 112:553-569 (1999)) and data dependent CID with dynamic exclusion (Goodlett et al., Anal. Chem. 15:1112-1118 (2000)) as the mass spectrometric method.

(viii) Database Searching. The sequence of all the peptides for which suitable CID spectra are obtained is determined by searching a sequence database from the species under investigation. A particularly useful sequence database is a database containing all the complete protein sequences that can be potentially expressed by the species under examination. The sequence database search program is the Sequest program (Eng, J. et al., J. Am. Soc. Mass. Spectrom. 5:976-989, (1994)) or a program with similar capabilities.

(ix) AP index (APT database) Construction. The sequences of all the peptides that have been identified by the procedure described above are entered in a database and annotated with the characteristics, or attributes, that were generated during steps (i)-(viii) above. These characteristics, or attributes, include, but are not limited to: partial amino acid composition (such as the presence of a cysteine residue in each selected peptide; see Goodlett et al., supra, 2000); the approximate molecular mass of the parent protein (as determined by the optional SDS-PAGE fractionation); the order of elution or elution time from the cation ion exchange column; and the elution time from the reversed-phase column. Collectively, these attributes are unique for every peptide in the database akin to a bar code for each peptide. Therefore, if the same bar code is being determined from the peptides generated in subsequent experiments, they will uniquely identify the peptides generated by the experiment, simply by correlating the bar codes generated by the experiment with the bar codes present in the AP index (APT database).

For correlation of polypeptides with the AP index (APT database), the peptide samples generated for quantitative proteome analysis by the method described above are generated, treated and processed precisely like the peptides generated for the AP index (APT database), with the following exceptions. (i) The proteins in the two (or more) samples to be compared are labeled with differentially isotopic labeled ICAT™ type reagents. Two or several chemically identical but differentially isotopically labeled ICAT™ type reagents can be used at this step. (ii) The generated peptides are analyzed by single stage mass spectrometry only, rather than by MS/MS. Mass analyzers will generally have a high mass accuracy, high sensitivity and high mass resolution. Instruments with these characteristics include, but are not limited to, MALDI-TOF mass spectrometers, ESI-TOF mass spectrometers and Fourier transform ion cyclotron mass analyzers (FT-ICR-MS). The attributes determined from each peptide by this process (all the attributes described above or a selection thereof) are translated into a bar code for each peptide, and the experimentally determined bar code is correlated with the bar codes from the AP index (APT database), resulting in the unambiguous identification of the peptide and therefore the protein from which the peptide originated. Subsequently, the mass spectra are examined for pairs of peptide ions that co-fractionated throughout the process and that have a mass difference that precisely corresponds to the mass difference encoded in the ICAT™ type reagent used. The relative signal intensities of the two peaks indicate the relative abundance of the peptides and therefore the relative abundance of the corresponding proteins initially present in the sample. Consequently, the correlation of the experimentally determined data with the AP index (APT database) allows quantification and identification of the proteins in the samples analyzed.

EXAMPLE II

Generation of a Yeast Annotated Polypeptide Index

This example describes the generation of an annotated polypeptide index for yeast.

At least 5 mg of total protein was estimated to be required at current mass spectrometer sensitivity to detect low abundance proteins using the LC/LC/MS/MS method (Gygi et al., Proc. Natl. Acad. Sci. USA 97:9390-9395 (2000)), and this amount was essentially experimentally confirmed. Gygi et al., supra, 2000 also demonstrated that the "binning" process is adequate for the detection of low abundance proteins and has sufficient sample capacity to accommodate the relatively large amounts of total sample.

For the construction of the database, the following procedure is used. For protein labeling, a protein sample is generated in 0.5% SDS, 50 mM Tris, pH 8.3, 5 mM ethylenediaminetetraacetic acid (EDTA) at a protein concentration of 5 mg/ml. A total of 25 mg of total yeast protein is used. Once proteins are in solution, the SDS concentration is lowered by diluting the sample 1:10 with water and adding EDTA to maintain a 5 mM EDTA concentration. The final concentration is 0.05% SDS, 5 mM Tris, 5 mM EDTA. The sample is then boiled for 3-5 min at 100° C. and then chilled. Reduction of disulfide bonds is accomplished by adding sufficient Tributylphosphine (TBP) to achieve 5 mM in the sample solution. This is followed by an incubation of the sample at 37° C. for 30 min. To the reduced sample, the alkylating reagent (e.g. ICAT™ type reagent) is added at an estimated 5× molar excess over the SH groups present in the sample. The alkylation reaction is allowed to proceed in darkness for 90 min.

For protein separation, the reduced and alkylated sample is added with 0.2 volume of 5×SDS gel sample buffer and boiled for 5 min. The cooled sample is then applied to a preparative SDS gel with the dimensions 20 cm×20 cm×1.5 mm. After electrophoresis, the gel is sliced perpendicular to the electrophoresis dimension into 10 strips of equal size. These strips represent 10 size bins for the intact proteins. The proteins in the gel strips are then subjected to in-gel digestion using standard protocols.

For peptide separation, the peptides that are extracted from the gel slices are subjected to three sequential chromatographic separations. First, they are separated by cation exchange chromatography. Second, the biotinylated peptides are isolated by avidin chromatography. Third, peptides are further fractionated by capillary reverse-phase chromatography.

For cation exchange chromatography, a cation exchange HPLC column is used (PolyLC Inc., 2.1 mm×20 cm, 5 (m particles, 300 Å pore size, Polysulfoethyl A strong cation exchange material). The following buffers are used: Buffer A, 10 mM $KH_2PO_4$, 25% $CH_3CN$, pH 3.0; Buffer B, 10 mM $KH_2PO_4$, 25% $CH_3CN$, 350 mM KCl, pH 3.0. The following gradient is run:

| Time (min) | % B |
|---|---|
| 0 | 0 |
| 30 | 25 |
| 50 | 100 |

The flow rate is 200 µL per minute. Fractions are collected at 1-2 minute intervals. Anywhere from about 200 microgram up to about 5 mg of digested, ICAT™ labeled total protein is loaded on this column, usually using a 2 mL sample loop. It is important to acidify the samples down to pH 3.0 or below before loading onto the cation exchange column because peptides will not be fully charged at higher pH values and can possibly not stick to the column. The gradient shown is designed to spread out the elution of doubly-charged peptides as much as possible, with these peptides usually eluting starting at about 8-9 minutes into the run until approximately minutes 15-16, after which triply charged peptides begin to elute. 30 fractions are collected over the duration of the gradient.

For avidin affinity chromatography, an Ultralink Monomeric Avidin (Pierce, cat # 53146) is used. A small piece of glass wool is packed into the neck of a glass pipette tube. 400 µavidin chromatography material is packed into the tube (slurry comes at 50% dilution, so 800 µl of 50% slurry is added in order to get 400 µl avidin chromatography material). The beads are allowed to settle, and the column is washed with 2×PBS to bring the beads down off the side of the tube. The packed column is washed through with 30% Acetonitrile (ACN) with 0.4% Trifluoroacetic acid (TFA) until the flow-through pH changes to ~1, and then another column volume of the ACN/TFA is washed through. This acidic step is to get rid of polymers associated with the beads. The column is washed with 2×PBS pH 7.2 until the pH is ~7.2. Thereafter, the column is washed through with 3 more column volumes (1200 µl) of same buffer.

The column is washed with 3-4 column volumes of biotin blocking buffer (2 mM d-biotin in PBS). This biotin blocks the more retentive avidin sites on the column, ensuring recovery of the sample from the remaining binding sites later on.

Loosely bound biotin is washed off with ~6 column volumes (2,400 µl) of regeneration buffer (100 mM glycine, pH 2.8), until the flow-through pH changes to ~2.8. This glycine solution is sterilized by autoclaving before use and stored at 4° C., where it will last one week.

The column is washed with 6 column volumes of 2×PBS to return column to proper pH (~7.2). The flow-through pH is monitored. The peptide samples consisting of individual or pooled ion exchange column fractions are then applied to the column and incubated in column for ~20 min. Unbound material is then washed from the column by applying 5 column volumes of 2×PBS, pH 7.2, and fractions are collected. The column is further washed through with 5× column volumes of 1×PBS (this step is to reduce the salt concentration), and 6 column volumes of 50 mM AMBIC, pH 8.3, with 20% methanol (MeOH) while continuing to collect fractions (50 mM AMBIC is to bring the salt concentration down; MeOH is to get rid of hydrophobic peptides). Biotinylated peptides are eluted with elution buffer (30% ACN/0.4% TFA) and collected manually in a glass tube. These samples are further separated by capillary reverse-phase chromatography.

For reverse-phase chromatography, purified biotinylated peptides are separated by reverse-phase capillary chromatography using standard protocols. The solvent gradient is chosen so that the peptides elute over 60 min. If 1 min fractions are collected and analyzed in the mass spectrometer, 60 bins are created by this procedure.

For mass analysis and sequencing, biotinylated peptides eluting from the RP-columns are analyzed by ESI-MS/MS for the generation of the database and by ESI-MS for database searching. For the database construction, an ion trap mass spectrometer is used with a mass accuracy of approximately 1 mass unit. For the mass measurement for database searching, an ESI-TOF mass spectrometer is used with a mass accuracy exceeding 50 ppm and a resolution exceeding 10.000. That means that a peptide at 1000 mass units can be distinguished from a peptide at 1000.1 mass units. If a mass range for tryptic peptides is assumed to be between 500 and 3000 mass units, a mass spectrometer at that performance would generate 25.000 bins.

In the case of proteome analysis of the yeast S. cerevisiae, the genome of this organism contains approximately 6200 ORF's. The yeast proteome therefore is expected to be approximately 6200 different proteins, disregarding differentially modified forms of the same protein. Tryptic digestion of a yeast proteome would yield approximately 350,000 peptides if empirically derived specificity rules for trypsin are applied. This sample complexity is reduced to approximately 35,000 peptides if only the cysteine-containing peptides are extracted, based on the chemical derivatization with the ICAT™ type reagents. The total number of bins available from the procedure described above is $10 \times 30 \times 60 \times 25.000 = 4.5 \times 10^6$ and therefore by far exceeds the number of peptides expected from a total yeast proteome analysis. It is therefore expected that for a sample of the complexity of a yeast extract, the procedure for the generation of database search data can be simplified. As an example, the gel electrophoresis sizing step for proteins can be optionally eliminated.

Neither the procedure for the generation of the data to be entered into the database nor the procedure for the generation of data to search the database are fixed. Therefore, for optimization, depending on the degree of sample complexity, the number of bins available can be easily adjusted. Generally, the number of bins chosen for the generation of the database is high, whereas the number of bins for generating the database search data would be chosen as low as possible to maximize the sample throughput. The number of bins available can be easily adapted in various ways. Firstly, the inclusion of additional orthogonal separation dimensions can be considered for proteins or peptides. For protein separation, isoelectric focusing, ion exchange chromatography, hydroxylapatite chromatography, or similar electrophoretic or chromatographic techniques can be included. For peptide separation, separation based on peptide size or capillary electrophoresis methods can be included.

Secondly, the separation range for the separation methods described above can be extended. Protein sizing can be extended by using gradient gels or longer gels with extended separation range. For the chromatographic peptide separation methods, the number of bins can be easily expanded by generating extended, shallower gradients and/or by sampling more frequently. Finally the number of bins is critically dependent on the resolution and mass accuracy of the mass analyzer used. Adding a mass analyzer with higher performance will decrease the number of bins provided by the separation methods employed in the procedure.

EXAMPLE III

Use of ESI-TOF for MS Analysis of Complex Samples

This example describes a method for determining a polypeptide identification subindex using the mass of polypeptide fragments determined by ESI-TOF.

The masses of a set of polypeptides, or fragments thereof, were determined using ESI-TOF in order to constrain a polypeptide identification index by mass values to generate a polypeptide identification subindex for use with complex genomes. Two peptides, ASHLAGAR (SEQ ID NO: 1)(P1) and RPPGFSPFR (SEQ ID NO: 2) (P2), were infused together into an ESI-TOF. The mixture was intended to simulate co-elution of peptides during HPLC separation. Spectra were acquired at low (FIG. 4A) and high (FIG. 4B) $V_{Nozzle\text{-}Skimmer}$.

Figures 4A, 4B:
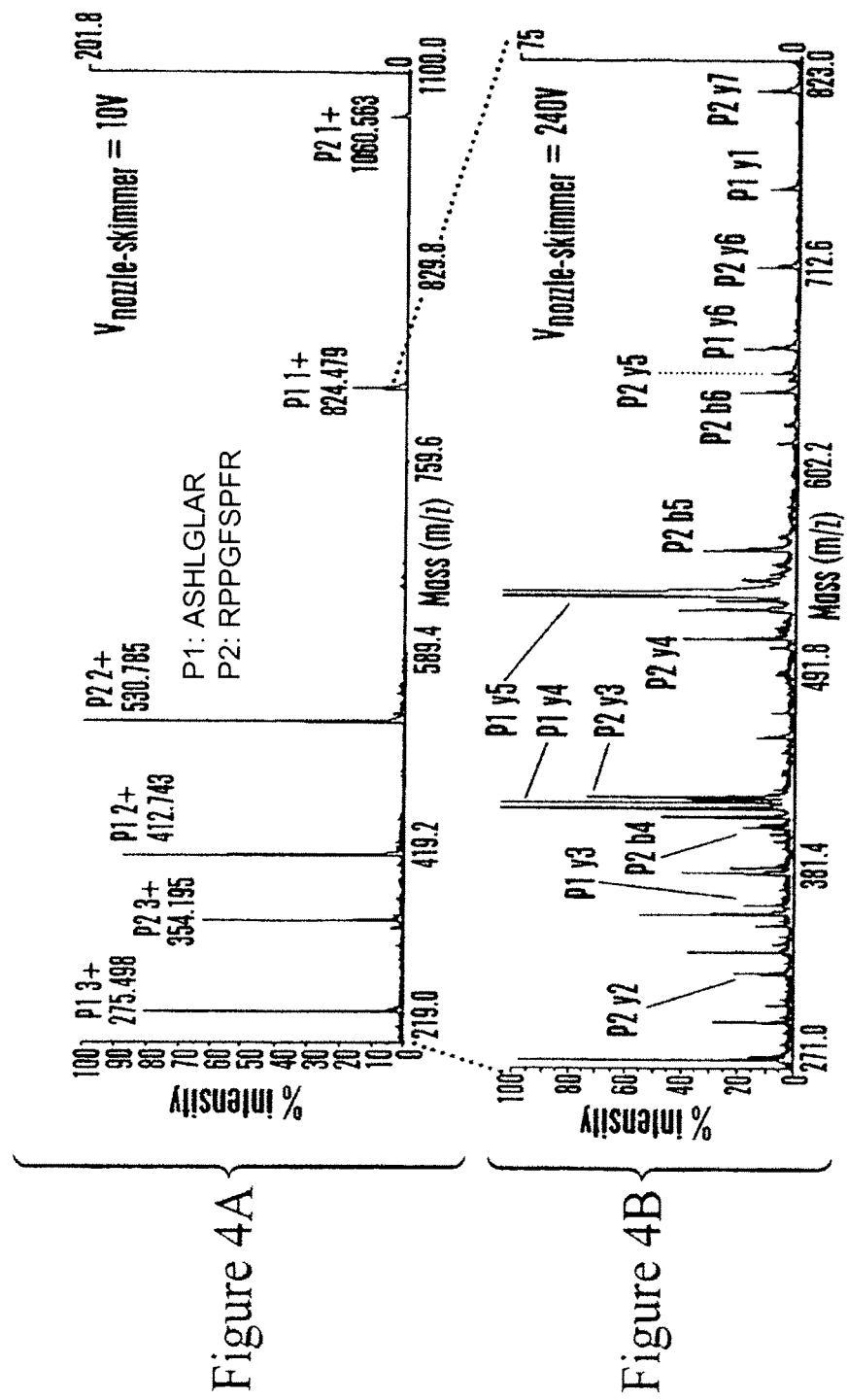
FIGS. 4A and 4B show mass spectra of two polypeptides (P1 and P2) obtained using ESI-TOF. Spectra were acquired at low $V_{Nozzle\text{-}Skimmer}$ (10V) (FIG. 4A) and high $V_{Nozzle\text{-}Skimmer}$ (240V)(FIG. 4B).

As can be seen in FIG. 4B there are numerous fragment ions present for both peptides. No fragment ions appeared above the P1 1+ ion and so this m/z range was omitted from FIG. 4B. An algorithm was written to deconvolute the mixture of parent and fragment ions in a single mass spectrum (FIG. 4B). P1 and P2 sequences were placed into a list of all possible tryptic peptides from the database of 60884 human polypeptides. Comparison of P1 and P2 observed masses (FIG. 4A) to all possible tryptic peptides from the 60884 polypeptides, produced a list of 57 and 124 isobars, respectively. The list of b- and y-ion fragments from all isobars calculated to 10 ppm was then compared to the observed fragment ions between 500 and 825 m/z in FIG. 4B. This process produced a list of 12 and 13 possible polypeptide identifications for P1 and P2, respectively, as shown in FIG. 4C. This method is useful for applying a constraint to a polypeptide identification index to generate a polypeptide identification subindex for use with complex genomes. In-source CID on peptides can be acquired easily and quickly in a continuously alternating fashion by ESI-TOF and potentially by in-source decomposition in MALDI-TOF. Furthermore, the method does not result in loss of data as occurs with tandem MS where, during CID of a selected ion, co-eluting ions are necessarily omitted from analysis. If the peptides are of low abundance (i.e. low signal-to-noise) then they will not be selected for CID by data dependent (DD) tandem MS processes. This is because standard DD processes examine first the base peak (i.e., most intense ion per m/z window), carries out CID on it, dynamically excludes it from further consideration, and proceeds to the next most abundant ion.

The peptides shown in FIG. 4C represent a reduction in complexity from over 60,000 possible polypeptides to about 12 or 13 polypeptides. Additional characteristics are determined, for example, atomic mass, amino acid composition, partial amino acid sequence, apparent molecular weight, pI, and order of elution on specific chromatographic media under defined conditions, and the like, for parent polypeptides or one or more additional peptide fragments thereof. Methods for fractionating polypeptides have been previously described (see, for example, Scopes, *Protein Purification: Principles and Practice,* 3rd ed., Springer Verlag, New York (1993)). A sufficient number of characteristics are determined so that a single polypeptide in the polypeptide identification index is identified.

Throughout this application various publications have been referenced. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method of mass spectrometry for identifying a plurality of polypeptides in a sample, said method comprises the steps of:
   subjecting the sample comprising a plurality of parent polypeptides to a mass spectrometer;
   mass analyzing said polypeptides by continuously alternating the mass spectrometer between:
   (i) a parent ion scan mode of operation including generating a first mass spectrum by mass analyzing a plurality of parent polypeptide ions of different masses; and
   (ii) a Collision Induced Dissociation (CID) scan mode of operation including simultaneously fragmenting a plurality of parent polypeptide ions of different masses without selecting a specific ion to form resulting fragment ions and then generating a second mass spectrum by mass analyzing the resulting fragment ions;
   determining the masses of said parent polypeptide ions from the first mass spectrum generated in step (i);
   determining the masses of said fragment ions from the second mass spectrum generated in step (ii);
   comparing the masses of said parent polypeptide ions and the masses of said fragment ions to an annotated polypeptide index; and
   identifying one or more of the plurality of parent polypeptides in said sample on the basis of comparison.

2. The method of claim 1, further comprising quantitating the amount of an identified polypeptide in a sample containing said polypeptide.

3. The method of claim 1, further comprising measuring the relative abundance in two or more different populations of polypeptides.

4. The method of claim 1, further comprising determining one or more additional characteristics associated with one or more parent polypeptides.

5. The method of claim 4, wherein said step of comparing the mass of said parent ions and the mass of said fragment ions to an annotated polypeptide index further comprises comparing one or more additional characteristics associated with one or more parent polypeptides to said annotated polypeptide index.

6. The method of claim 4, wherein said one or more additional characteristics comprises amino acid composition.

7. The method of claim 4, wherein said one or more additional characteristics comprises pI.

8. The method of claims 4, wherein said one or more additional characteristics comprises order of elution on a chromatographic medium.

9. The method of claim 1, wherein said fragment ions are mass analyzed to an accuracy in ppm of 1 ppm or greater ppm.

10. The method of claim 1, wherein said fragment ions are mass analyzed to an accuracy in ppm of 2.5 ppm or greater ppm.

11. The method of claim 1, wherein said fragment ions are mass analyzed to an accuracy in ppm of 5 ppm or greater ppm.

12. The method of claim 1, wherein said fragment ions are mass analyzed to an accuracy in ppm of 10 ppm or greater ppm.

13. The method of claim 1, wherein said fragment ions are mass analyzed to an accuracy in ppm of 100 ppm or greater ppm.

* * * * *

SEQUENCE LISTING

<160> NUMBER OF SEQ ID NOS: 25

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ser His Leu Gly Leu Ala Arg
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Pro Pro Gly Phe Ser Pro Phe Arg
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Cys Ile Ser Glu Ile Leu Pro Ser Lys
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Val Arg Tyr Ser Phe Gly Phe Lys
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Asn Leu Ile Ser Gln Cys Arg
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 6

Arg Cys Gly Leu Pro Ser Ser Gly Lys Arg
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Asp Ile Thr Leu Glu Ala Ser Arg
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Glu Arg Glu Thr Leu Glu Lys
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Leu Thr Glu Glu Glu Arg Lys
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Leu Val Glu Val Asp Ser Ser Arg
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Asn Leu Leu Asp His His Arg
1               5

<210> SEQ ID NO 12

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Pro His Ala Ala Gln Pro Gly Ala Arg
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Pro Gln Thr Ala Thr Ala Ser Thr Lys
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Arg Pro Ser Ala Tyr Gln Ala Leu
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Cys Tyr Ile Lys Val Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Asp Pro Leu Pro Arg Arg
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17
```

```
Ala Phe Val Ala Phe Ala Ala Lys
1               5
```

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Ala Phe Val Phe Gly Arg Lys
1               5
```

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Ala His Ala Glu Ile Arg Lys
1               5
```

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Ala His Glu Ala Lys Ile Arg
1               5
```

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Ala Leu Glu Ala His Lys Arg
1               5
```

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Ala Leu Gln Phe Phe Ala Lys
1               5
```

<210> SEQ ID NO 23
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 23

Ala Met Ala Ile Tyr Lys Lys
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Pro Asp Pro Arg Leu Arg
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Val Ala Gly His Leu Thr Arg
1               5
```